United States Patent [19]

Howell

[11] Patent Number: 4,616,082
[45] Date of Patent: Oct. 7, 1986

[54] HYDROQUINONE ETHER COMPOUNDS

[75] Inventor: Frederick H. Howell, Atherton, England

[73] Assignee: Ciba-Geigy AG, Basel, Switzerland

[21] Appl. No.: 743,473

[22] Filed: Jun. 7, 1985

Related U.S. Application Data

[62] Division of Ser. No. 504,283, Jun. 14, 1983, Pat. No. 4,549,015.

[30] Foreign Application Priority Data

Jun. 16, 1982 [GB] United Kingdom ............... 8217445
Dec. 15, 1982 [GB] United Kingdom ............... 8235665

[51] Int. Cl.$^4$ ............ C07C 43/205; C07C 43/23; C07D 265/30
[52] U.S. Cl. ................. 544/87; 562/426; 562/465; 260/507 R; 562/478; 564/83; 260/511; 564/85; 564/86; 260/512 R; 564/88; 564/89; 260/543 R; 564/123; 564/154; 544/173; 564/158; 564/170; 546/240; 564/185; 564/192; 549/406; 564/337; 564/374; 549/408; 564/382; 568/636; 549/462; 568/638; 568/640; 560/1; 568/644; 560/9; 560/55; 560/75; 560/105; 560/106; 560/107; 560/221; 560/254; 560/255; 568/648; 568/650; 568/654; 568/636; 568/638; 568/640; 568/644; 562/426; 562/465; 562/478; 564/83; 564/85; 564/86
[58] Field of Search ............ 260/507 R, 511, 512, 260/543 R; 544/87, 173; 546/240; 548/582; 549/406, 408, 462; 560/1, 9, 55, 75, 105, 106, 107, 221, 254, 255; 562/426, 465, 478; 564/123, 154, 158, 170, 185, 192, 337, 374, 382, 83, 85, 86, 88, 89; 568/636, 638, 640, 644, 646, 648, 650, 654

[56] References Cited

U.S. PATENT DOCUMENTS 3,166,562 1/1965 Leditschke et al. ........... 564/382 X
3,997,608 12/1976 Suh .......................... 564/382 X
4,139,545 2/1979 Morimoto et al. ............. 260/396 R
4,388,312 6/1983 Terao et al. .................. 424/244

4,484,000 11/1984 Howell ........................ 560/75

FOREIGN PATENT DOCUMENTS 2412798 9/1974 Fed. Rep. of Germany.
2952549 10/1980 Fed. Rep. of Germany.
1125619 8/1968 United Kingdom.

OTHER PUBLICATIONS

Ehrhart, Ber., vol. 97(1) 1964, pp. 74-78.
Bruce et al., J. Chem. Soc., Perkin Trans 1, 1972 (3), pp. 372-379.
Aldous et al., J. Med. Chem., vol. 17(10), 1974, pp. 1100-1111.

Primary Examiner—Richard L. Raymond
Attorney, Agent, or Firm—Wenderoth, Lind & Ponack

[57] ABSTRACT

New hydroquinone ether compounds of formula I are described:

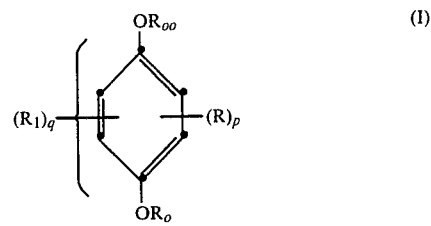

wherein p is 1 or 2 and Q is 0 or 1, provided that p+q is 1 or 2, R is a residue of formula II

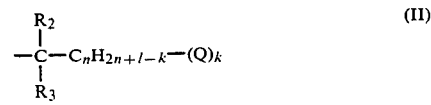

and $R_o$, $R_{oo}$, $R_1$, $R_2$, $R_3$, Q, n and k are as defined in the specification, The new compounds are useful e.g. as stabilizers in photographic material.

10 Claims, No Drawings

HYDROQUINONE ETHER COMPOUNDS

This application is a division of application Ser. No. 504,283, filed June 14, 1983, now U.S. Pat. No. 4,549,015.

The present invention relates to new hydroquinone compounds, especially functionally alkylated hydroquinone ethers useful in photographic systems.

Hydroquinone derivatives containing functional groups are described for example in the GB-patent specification No. 1 465 082 (monoalkylated hydroquinone compounds) and in the JP-patent application publication No. 54/73032 (hydroquinone diethers).

According to the present invention, there are provided compounds having the formula I

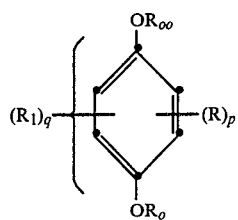

wherein p is 1 or 2 and q is 0 or 1, provided that p+q is 1 or 2; R is a residue of formula II

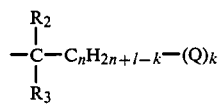

wherein Q is selected from the residues:
(i) —COZR$_4$ wherein Z is —O— or

and R$_4$ independently is H, a C$_1$-C$_{20}$ straight or branched chain alkyl optionally interrupted by 1 to five oxygen atoms and optionally substituted by a group—OR$_6$ wherein R$_6$ is C$_3$-C$_{12}$ cycloalkyl, straight or branched C$_3$-C$_{20}$ alkenyl, C$_6$-C$_{10}$ aryl optionally substituted by one or two C$_1$-C$_4$ alkyl groups, or C$_7$-C$_{13}$ aralkyl, or R$_4$ is a divalent C$_2$-C$_{20}$ straight or branched chain alkylene residue, a C$_3$-C$_{20}$ straight or branched chain alkenyl group or a C$_3$-C$_{12}$ cycloalkyl group; a C$_6$-C$_{10}$ aryl group optionally substituted by one or two C$_1$-C$_8$ alkyl groups or a C$_7$-C$_{13}$ aralkyl group; a 5 or 6 membered heterocycle containing an oxygen atom, and optionally substituted by one or two C$_1$-C$_4$ straight or branched chain alkyl groups; or methyl substituted by a 5 or 6 membered heterocycle containing an oxygen atom and optionally substituted by one or two C$_1$-C$_4$ straight or branched chain alkyl groups; and when Z is —NR$_5$, R$_5$ is hydrogen, a C$_1$-C$_{20}$ straight or branched chain alkyl group, or a C$_5$-C$_6$ cycloalkyl group, or R$_4$ and R$_5$, together with the nitrogen atom to which they are each bonded, may form a 5 or 6 membered heterocyclic ring, optionally substituted by one or two C$_1$-C$_4$ alkyl groups;

(ii) —OX wherein X is R$_7$ or —COR$_7$, wherein R$_7$ is —H or a C$_1$-C$_{20}$ straight or branched chain alkyl group, a C$_3$-C$_{20}$ straight or branched chain alkenyl group, a C$_3$-C$_{12}$ cycloalkyl group, a C$_7$-C$_{13}$ aralkyl group, or a C$_6$-C$_{10}$ aryl group, optionally substituted by one or two C$_1$-C$_4$ alkyl groups;

(iii) —N(R$_8$)(R$_9$) wherein R$_8$ and R$_9$ independently are —H or a C$_1$-C$_{20}$ straight or branched chain alkyl group, a C$_3$-C$_{20}$ straight or branched chain alkenyl group, a C$_3$-C$_{20}$ cycloalkyl group, a C$_7$-C$_{13}$ aralkyl group, or a C$_6$-C$_{10}$ aryl group optionally substituted by one or two C$_1$-C$_4$ alkyl groups, or R$_9$ is an acyl group of formula —COR$_7$ wherein R$_7$ has its previous significance, or R$_8$ and R$_9$, together with the nitrogen atom to which they are each bonded, form a 5- or 6-membered heterocyclic ring, optionally substituted by one or two C$_1$-C$_4$ alkyl groups;

(iv) —PO(OR$_{10}$)([O]$_x$R$_{11}$) wherein x is 0 or 1, and when x is 1 R$_{10}$ and R$_{11}$ are the same or different and each is —H or a C$_1$-C$_{20}$ straight or branched chain alkyl group or a C$_6$-C$_{10}$ aryl group optionally substituted with one or two C$_1$-C$_4$ alkyl groups; or R$_{10}$ and R$_{11}$ may be linked together to form a C$_2$-C$_3$ alkylene chain optionally substituted by one to four C$_1$-C$_{20}$ alkyl groups; and when x is 0, R$_{10}$ has its previous significance and R$_{11}$ is a C$_1$-C$_5$ straight chain alkyl group;

(v) —SO$_2$R$_{12}$ wherein R$_{12}$ is —OH, —Cl or —N(R$_5$)(R$_7$) wherein R$_5$ and R$_7$ have their previous significance; provided that, when R$_{12}$ is —OH, then R$_1$ is a residue of formula II;

(vi) —CN, halogen or —NO$_2$; and (vii) —COR$_{15}$ wherein R$_{15}$ is —H or a C$_1$-C$_{20}$ straight or branched alkyl group or halogen; n is an integer from 1 to 20; k is 1 or 2; R$_2$ and R$_3$ are the same or different and each is straight or branched chain alkyl group having from 1 to 5 carbon atoms and, when Q is —CO$_2$R$_4$, either R$_2$ or R$_3$ is optionally substituted by a —CO$_2$R$_4$ group, the R$_4$ groups being independent, or when Q is —COOR$_4$ R$_2$ or R$_3$ may be so linked to the residue C$_n$H$_{2n}$—COOR$_4$ that there is formed a C$_5$-C$_{12}$ cycloalkylene residue optionally substituted by another group —CO$_2$R$_4$, the R$_4$ groups being independent, wherein R$_4$ has its previous significance, or when Q is —COR$_{15}$ R$_2$ or R$_3$ may be so linked to the residue C$_n$H$_{2n}$—COR$_{15}$ that there is formed a C$_5$-C$_{12}$ cycloalkylene residue wherein R$_{15}$ has its previous significance, provided that, when the group Q is a —CO$_2$R$_4$ residue wherein R$_4$ is a divalent C$_2$-C$_{20}$ straight or branched chain alkylene residue, then p and k are both 1 and the compound of formula I has the formula Ia:

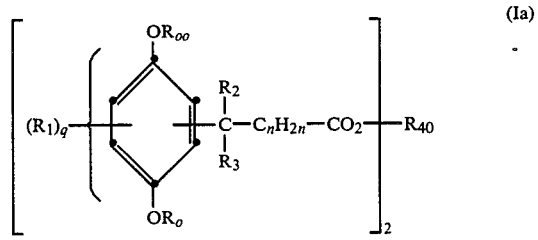

wherein R$_{40}$ is a C$_2$-C$_{20}$ divalent straight or branched chain alkylene residue; and provided that, when the group Q is —CON(R$_4$)(R$_5$) residue wherein R$_4$ is a C$_2$-C$_{20}$ divalent straight or branched chain alkylene residue and R$_5$ has its previous significance, then p and k are both 1 and the compound of formula I has the formula Ib:

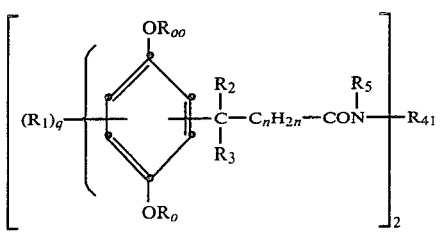
(Ib)

wherein $R_2$, $R_3$, q and n have their previous significance, $R_{41}$ is a $C_2$-$C_{20}$ divalent straight or branched chain alkyl residue; $R_1$ is $C_1$-$C_8$ straight or branched chain alkyl, $C_5$-$C_7$ cycloalkyl optionally substituted by one or two methyl or ethyl groups, $C_7$-$C_9$ aralkyl or a residue of formula II as hereinbefore defined, and when $R_1$ is a residue of formula II then $R_1$ and R may be the same or different; or $R_1$ is a residue of formula III:

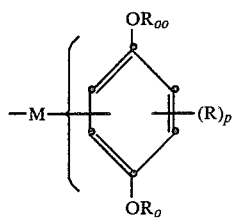
(III)

in which R and p have their previous significance; and M is a direct bond, —C($R_{13}$)($R_{14}$)— which $R_{13}$ and $R_{14}$ are the same or different and are hydrogen, $C_1$-$C_{20}$ straight or branched chain alkyl optionally interrupted by 1 to 3 sulphur atoms, $C_6$-$C_{10}$ aryl or $R_{13}$ and $R_{14}$, together with the carbon atom to which they are attached may form a 5- or 6-membered ring which may be further substituted by one or two $C_1$-$C_8$ straight or branched chain alkyl groups; —S—; —S—S—; —SO$_2$—; —CH$_2$SCH$_2$—; —CH$_2$OCH$_2$— or —C(CH$_3$)$_2$-p-phenylen-C(CH$_3$)$_2$—; $R_o$ and $R_{oo}$ are the same or different and each is hydrogen, a $C_1$-$C_{20}$ straight or branched chain alkyl group optionally interrupted by 1 to 5 oxygen atoms, a cycloalkyl group having 3 to 12 carbon atoms, a $C_6$-$C_{10}$ aryl group optionally substituted by one or two $C_1$-$C_4$ straight or branched chain alkyl groups or a $C_7$-$C_{13}$ aralkyl group provided that $R_o$ and $R_{oo}$ are not both hydrogen, or $R_{oo}$ has its previous significance and $R_o$ is a residue of formula IV

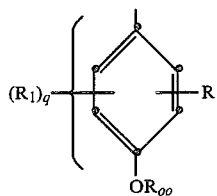
(IV)

in which R, $R_{oo}$, $R_1$ and q have their previous significance, or $R_o$ and $R_1$ when in ortho-position to one another, together with the carbon atoms to which they are attached may form an optionally substituted residue of formula V

(V)

wherein A is a carbon residue containing 4 to 20 carbon atoms which forms a substituted chroman or coumaran system, or $R_o$ and $R_1$ together may form a residue having the formula VI or VII:

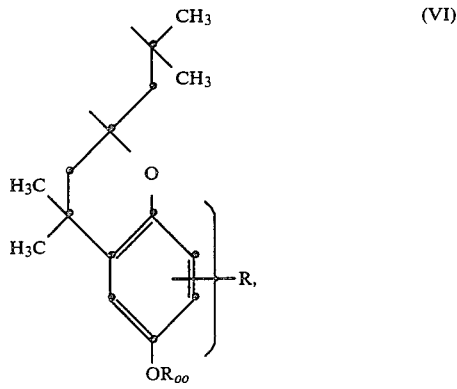
(VI)

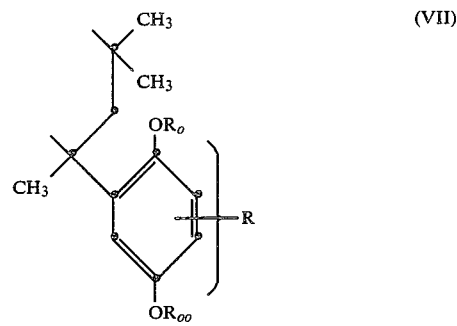
(VII)

wherein R, $R_o$ and $R_{oo}$ have their previous significance, provided that the compound of formula I contains only one residue of formula III or IV; or $R_{oo}$ is hydrogen and $R_o$ is a residue having the formula IVa or IVb:

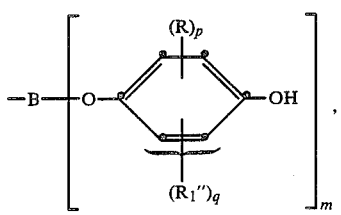
(IVa)

—CH($C_rH_{2r}$)—CO—D
|
$R_{16}$
(IVb)

wherein p, q and R have their previous significance, $R_1''$ is $C_1$-$C_8$ straight or branched alkyl, $C_7$-$C_9$ aralkyl or a residue of formula II, as hereinbefore defined, m is 1 or 2, B, when m is 1, represents $C_2$-$C_{12}$ alkylene which may be interrupted by 1 to 3 oxygen or sulphur atoms, $C_4$-$C_{10}$ alkylene, $C_5$-$C_{12}$ cycloalkylene, $C_6$-$C_{12}$ arylene, $C_8$-$C_{12}$ aralkylene, $C_{4-6}$ alkynylene, xylylene, —CH$_2$CH(OH)CH$_2$—, —CH$_2$CH(OH)CH$_2$—O—Y—O—CH$_2$CH(OH)CH$_2$—,

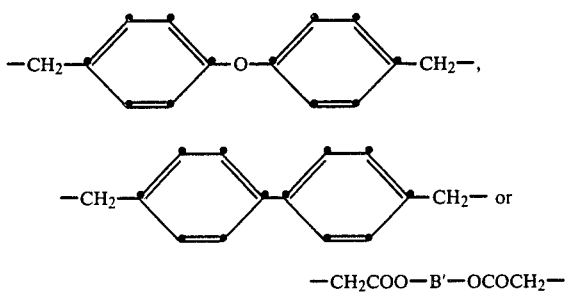

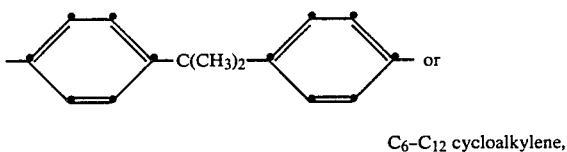

wherein Y is $C_2$–$C_{10}$ alkylene, $C_6$–$C_{12}$ arylene,

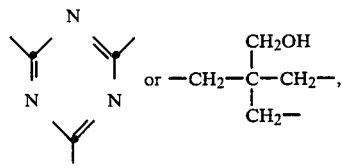

$C_6$–$C_{12}$ cycloalkylene,

B' is $C_2$–$C_8$ alkylene, $C_4$–$C_8$ oxyaalkylene, or cyclohexylene and, when m is 2, B represents a group of the formula $$\underset{N}{\overset{N}{\underset{\|}{Y}}}\underset{N}{\overset{}{\underset{}{Y}}}\quad \text{or} \quad -CH_2-\underset{CH_2-}{\overset{CH_2OH}{\underset{|}{C}}}-CH_2-,$$

r is 0 to 12, preferably 0, $R_{16}$ represents hydrogen or straight or branched $C_1$–$C_{12}$ alkyl and D is —$OR_4$ or —$N(R_4)(R_5)$ wherein $R_4$ and $R_5$ have their previous significance; as well as salts of compounds of formula I with bases or organic or inorganic acids, respectively, when Q is an acidic or basic group.

When the group $R_1$ is a $C_1$–$C_8$ straight or branched chain alkyl group it may be, for example, methyl, ethyl, n-propyl, isopropyl, n-butyl, iso-butyl, t-butyl, t-pentyl or 1,1,3,3-tetramethylbutyl.

When the group $R_2$ or $R_3$ is a $C_1$–$C_5$ straight or branched chain alkyl group it may be, for example, a methyl, ethyl, n-propyl, iso-propyl, n-butyl, sec-butyl, n-pentyl or neopentyl group.

When the group $R_4$, $R_o$ or $R_{oo}$ is a $C_1$–$C_{20}$ straight or branched chain alkyl group optionally interrupted by one to 5 oxygen atoms it may be, for example, a methyl, ethyl, 2-methoxyethyl, 2-ethoxyethyl, 2-n-propoxyethyl, 2-n-butoxyethyl, n-pentyl, n-hexyl, n-heptyl, n-octyl, 2-ethylhexyl, n-nonyl, n-decyl, n-dodecyl, n-tetradecyl, n-hexadecyl, n-octadecyl, n-eicosyl, —$(C_2H_4O)_2CH_3$, —$(C_2H_4O)_3CH_3$, —$(C_2H_4O)_4CH_3$ or —$(C_2H_4O)_5CH_3$ group.

When $R_4$, $R_6$, $R_7$, $R_8$ or $R_9$ is a $C_3$–$C_{20}$ straight or branched chain alkenyl group, it may be for example, a prop-2-enyl, n-but-2-enyl, 2-methyl-prop-2-enyl, n-pent-2-enyl, n-hex-2-enyl, n-hexa-2,4-dienyl, n-dec-10-enyl, or n-eicos-2-enyl group.

When the group $R_4$, $R_6$, $R_7$, $R_8$, $R_9$, $R_o$ or $R_{oo}$ is a $C_3$–$C_{12}$ cycloalkyl group, it may be, for example, a cyclopropyl, cyclobutyl, cyclopentyl, cyclohexyl, cyclooctyl, cyclodecyl, adamantyl, or cyclododecyl group. When the group $R_5$ is a $C_5$–$C_6$ cycloalkyl group it may be a cyclopentyl or cyclohexyl. When the group $R_4$, $R_6$, $R_7$, $R_8$, $R_9$, $R_o$ or $R_{oo}$ is a $C_7$–$C_{13}$ aralkyl group it may be, for example, a benzyl, phenylethyl, benzhydryl, or naphthylmethyl group. When the group $R_1$ is a $C_7$–$C_9$ aralkyl group, it may be e.g. a cumyl group. When the group $R_4$ is a $C_6$–$C_{10}$ aryl group optionally substituted by one or two $C_1$–$C_8$-straight or branched chain alkyl groups, it may be a phenyl, tolyl, xylyl, cumyl, butylphenyl, phenyl substituted by 1 or 2 1,1,3,3-tetramethylbutyl groups or naphthyl group.

When the group $R_6$, $R_7$, $R_8$, $R_9$, $R_{10}$, $R_{11}$, $R_o$ or $R_{oo}$ is a $C_6$–$C_{10}$ aryl group optionally substituted by one or two $C_1$–$C_4$ straight or branched chain alkyl groups, it may be, a phenyl, tolyl, xylyl, cumyl, butylphenyl or naphthyl group.

When the group $R_4$ is a 5- or 6-membered heterocycle containing oxygen, and optionally substituted by one or two straight or branched chain $C_1$–$C_4$ alkyl groups, it may be, for example, tetrahydrofuran-3-yl, tetrahydropyran-4-yl or 2,6-dimethyl-tetrahydropyran-4-yl. When the group $R_4$ is methyl substituted by a 5- or 6-membered heterocycle containing an oxygen atom, and optionally substituted by one or two straight or branched chain $C_1$–$C_4$ alkyl groups, it may be, for example, furfuryl, tetrahydrofurfuryl or tetrahydropyran-2-yl-methyl.

When the groups $R_4$ and $R_5$, and the groups $R_8$ and $R_9$, together with the nitrogen atom to which they are bonded form a 5- or 6-membered heterocyclic ring, optionally substituted by one or two $C_1$–$C_4$ alkyl groups, this ring may be for example a pyrrolidine, piperidine, morpholine or a 2,5-dimethyl morpholine ring.

When the groups $R_5$, $R_7$, $R_8$, $R_9$, $R_{10}$, $R_{11}$, $R_{13}$, $R_{14}$, $R_{15}$, $R_o$ or $R_{oo}$ are $C_1$–$C_{20}$ straight or branched chain alkyl they may be the same or different and may be methyl, ethyl, n-propyl, iso-propyl, n-butyl, sec-butyl, n-pentyl, n-hexyl, n-heptyl, n-octyl, 2-ethylhexyl, n-nonyl, n-decyl, n-dodecyl, n-tetradecyl, n-hexadecyl, n-octadecyl or n-eicosyl groups. Preferred alkyl groups $R_o$ and $R_{oo}$ are those containing 1 to 8 carbon atoms, optionally interrupted by 1 or 2 oxygen atoms.

When the groups $R_{10}$ and $R_{11}$ are linked to form a $C_2$–$C_3$ methylene chain optionally substituted by one to four $C_1$–$C_{20}$ alkyl chains, they may be for example —$CH_2CH_2$—, —$CH_2$—$CH_2$—$CH_2$—, —$CH_2CH(CH_3)$—, —$CH_2CH(C_2H_5)$—, —$CH_2CH(C_{20}H_{41})$—, —$CH(CH_3)CH(CH_3)$—, —$CH(CH_3)C(CH_3)_2$—, —$C(CH_3)_2C(CH_3)_2$—, —$CH_2CH_2$—$C(CH_3)_2$—, or —$CH(CH_3)CH_2CH(CH_3)$— groups.

When the groups $R_{13}$ and $R_{14}$ are linked to form a $C_4$- or $C_5$-alkylene chain optionally substituted by one or two $C_1$–$C_8$ alkyl chains, they may be e.g. —$(CH_2)_4$—, —$(CH_2)_5$—, —$CH_2CH_2$—$C(CH_3)$—$CH_2CH_2$—, —$CH_2CH_2$—$CH(t$—$C_4H_9)$—$CH_2CH_2$— or —$CH_2CH_2CH(CH_3)CH_2CH(CH_3)$—.

When the groups $R_o$ and R, together with the ring to which they are attached, form a substituted chroman or coumaran ring, they may be e.g. a 2,2,4-trimethyl- or 2,2-dimethyl-4-isopropyl chroman or 2,2-dimethylcoumaran.

When the group B is a $C_2$–$C_{22}$ alkylene chain optionally interrupted by one to three O- or S-atoms it may be e.g. —$(CH_2)_2$—, —$(CH_2)_3$—, —$(CH_2)_4$—, —$(CH_2)_6$—, —$(CH_2)_8$—, —$(CH_2)_{10}$—, —$(CH_2)_{16}$—, —$(CH_2)_{22}$—, —$CH_2CH_2OCH_2CH_2$—, —$CH_2CH_2(OCH_2CH_2)_2$—, —$CH_2CH_2(OCH_2CH_2)_3$— or —$CH_2CH_2SCH_2CH_2$—.

When the group B is a C$_4$–C$_{10}$ alkenylene chain it may be e.g. —CH$_2$CH=CH—CH$_2$—, —CH$_2$CH=CH—CH=CH—CH$_2$—, —(CH$_2$)$_4$CH=CH(CH$_2$)$_4$—.

When the group B is a C$_5$–C$_8$ cycloalkylene group it may be e.g. 1,1-cyclohexylene, 1,2-cyclohexylene or 1,4-cyclohexylene.

When the groups B and Y are C$_6$–C$_{12}$ arylene they may be e.g. a 1,2-phenylene, 1,4-phenylene, or 4,4'-biphenylene.

When the group B is a C$_8$–C$_{12}$ aralkylene it may be e.g.

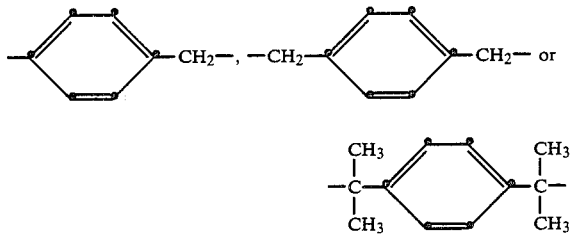

When the group B is a C$_4$–C$_6$ alkynylene it may be for example —CH$_2$—C≡C—CH$_2$—, or —C≡C—C≡C—.

When the group Y is a C$_2$–C$_{10}$ alkylene, it may be e.g. —(CH$_2$)$_2$—, —(CH$_2$)$_3$—, —(CH$_2$)$_4$—, —(CH$_2$)$_6$—, —(CH$_2$)$_8$— or —(CH$_2$)$_{10}$—.

When the group Y is a C$_5$–C$_{12}$ cycloalkylene it may be e.g. 1,2-cyclohexylene, 1,3-cyclohexylene, 1,4-cyclohexylene, 1,2-cyclooctylene or 1,2-cyclododecylene.

When the group B' is a C$_2$–C$_8$ alkylene it may be e.g. —(CH$_2$)$_2$—, —(CH$_2$)$_3$—, —(CH$_2$)$_4$—, —(CH$_2$)$_6$— or —(CH$_2$)$_8$—.

When the group B' is a C$_4$–C$_8$ oxaalkylene group it may be e.g. —CH$_2$CH$_2$OCH$_2$CH$_2$—, or —CH$_2$CH$_2$(OCH$_2$CH$_2$)$_3$—.

When the group R$_{16}$ is a C$_1$–C$_{12}$ straight or branched chain alkyl group it may be, methyl, ethyl, n-propyl, isopropyl, butyl, sec.-butyl, n-pentyl, n-hexyl, n-heptyl, n-octyl, 2-ethylhexyl, n-nonyl, n-decyl or n-dodecyl group.

When the group R$_{15}$ or Q is a halogen it may be fluorine, chlorine or bromine.

Examples of salts where Q is an acidic group e.g. —COOH include salts with alkali and alkaline earth metals and amines and, where Q is a —N(R$_8$)(R$_9$) group, salts with organic and inorganic acids, for example, hydrochloric-, sulphuric-, para-toluene-sulphonic- and oxalic acids.

In one preferred embodiment, the groups R and R$_1$ are bonded in the 2- and 5-positions, respectively, in the hydroquinone ethers of formula I.

Other preferred compounds of the invention are those having the formula VIII:

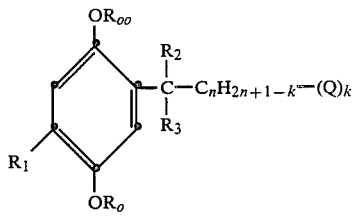

wherein R$_2$, R$_3$, R$_o$, R$_{oo}$, n, k and Q have their previous significance and R$_1$ is a group of formula II as hereinbefore defined, or is a group of formula IX:

wherein G is C$_1$–C$_5$ alkyl or phenyl as well as salts thereof.

Preferred compounds of formula VIII and their salts are those wherein R$_1$ is a group of formula II or IX, Q is —COZR$_4$ or —OR$_7$ in which Z, R$_4$, R$_5$ and R$_7$ have their previous significance, R$_2$ and R$_3$, independently, are methyl, ethyl, n-propyl, isopropyl or neopentyl; or either R$_2$ or R$_3$ is optionally substituted by a group —COOR$_4$ wherein R$_4$ has its previous significance, or R$_2$ or R$_3$ may be so linked to the residue C$_n$H$_{2n}$—COOR$_4$ that there is formed a cycloalkylene residue having 5 to 8 carbon atoms which is substituted by another —COOR$_4$; and R$_o$, R$_{oo}$, n and k have their previous significance; more particularly compounds of formula VIII wherein k is 1, R$_1$ is a group of formula II or IX, Q is —COZR$_4$ or —OR$_5$, n is an integer from 1 to 10, R$_2$ and R$_3$, independently, are methyl, ethyl or neopentyl, or one of R$_2$ and R$_3$ may be so linked to the residue —C$_n$H$_{2n}$—COOR$_4$ that there is formed a cyclohexylene residue which is substituted by —COOR$_4$, R$_4$ is hydrogen, C$_{1-20}$ alkyl, optionally interrupted by 1, 2 or 3 oxygen atoms and/or optionally substituted by —OR$_6$ wherein R$_6$ is cyclopentyl, cyclohexyl, cyclooctyl, C$_3$–C$_{10}$ alkenyl, phenyl, benzyl, phenethyl, benzhydryl or naphthylmethyl, or R$_4$ is C$_3$–C$_{15}$ alkenyl or phenyl optionally substituted by 1 or 2 C$_1$–C$_4$ alkyl groups, benzyl, phenethyl, cyclopentyl, cyclohexyl or a 5- or 6-membered heterocyclic ring containing an oxygen atom, which ring is optionally substituted by 1 or 2 C$_1$–C$_4$ alkyl groups, and Z, R$_o$, R$_{oo}$ and R$_7$ have their previous significance, or R$_4$ and R$_5$, together with the nitrogen atom to which they are each bonded, form a 5- or 6-membered heterocyclic ring, optionally substituted by one or two C$_1$–C$_4$ alkyl groups: as well as salts of these compounds.

Still further preferred compounds of formula VIII wherein k is 1, R$_1$ is a group of formula II or IX, Q is —COZR$_4$ or —OR$_7$, and their salts, are those wherein Z has its previous significance, n is an integer from 1 to 10, R$_2$ and R$_3$, independently, are methyl, ethyl or neopentyl, or one of R$_2$ and R$_3$ may be so linked to the residue —C$_n$H$_{2n}$—COOR$_4$ that there is formed a cyclohexylene residue which is substituted by —COOR$_4$, R$_4$ is C$_1$–C$_{20}$ alkyl optionally interrupted by 1 or 2 oxygen atoms and/or optionally substituted by cyclohexyloxy, C$_3$–C$_{10}$ alkenyloxy, phenoxy or benzyloxy, or R$_4$ is C$_3$–C$_{15}$ alkenyl, phenyl, benzyl, phenylethyl, cyclopentyl, cyclohexyl, a 5- or 6-membered heterocyclic ring containing an oxygen atom, or methyl substituted by a 5- or 6-membered heterocyclic ring containing an oxygen atom, and is especially C$_1$–C$_{16}$ alkyl optionally interrupted by an oxygen atom, or optionally substituted by phenoxy, or R$_4$ is C$_3$–C$_{15}$ alkenyl, phenyl, benzyl, tetrahydrofuran-3-yl or tetrahydrofurfuryl, R$_7$ is hydrogen or C$_1$–C$_{15}$ alkyl, or R$_4$ and R$_5$, together with the nitrogen atom to which they are each bonded, form a 5- or 6-membered heterocyclic ring optionally substituted by one or two C$_1$–C$_4$ alkyl groups, and R$_o$ and R$_{oo}$ are hydrogen or $C_1$–$C_8$ alkyl, optionally, but preferably not, interrupted by 1 or 2 oxygen atoms, cyclohexyl, phenyl or benzyl, or $R_o$ and $R_1$ together form a residue of formula V as hereinbefore defined.

Particularly preferred compounds of formula VIII and their salts are those wherein k is 1, $R_1$ is a group of formula II or IX, Q is —COZ$R_4$ or —OR$_7$ wherein Z has its previous significance, n is an integer from 1 to 3, $R_2$ and $R_3$ are each methyl or neopentyl, $R_4$ is $C_1$–$C_{16}$alkyl optionally interrupted by an oxygen atom or optionally substituted by phenoxy, or $R_4$ is $C_3$–$C_{15}$alkenyl, phenyl, benzyl, tetrahydrofuran-3-yl or tetrahydrofurfuryl, $R_7$ is hydrogen or $C_1$–$C_{15}$alkyl or $R_4$ and $R_5$, together with the nitrogen atom to which they are each bonded, form a 5- or 6-membered heterocyclic ring optionally substituted by one or two $C_1$–$C_4$alkyl groups, and $R_o$ and $R_{oo}$ are hydrogen or $C_1$–$C_4$alkyl, or $R_o$ and $R_1$ together form a residue of formula V as hereinbefore defined, provided that when Q is —OR$_7$, $R_7$ is, in particular, $C_1$–$C_8$ alkyl.

Preferably, one of $R_o$ and $R_{oo}$ is hydrogen and the other is $C_1$–$C_4$alkyl, or $R_o$ and $R_1$ together form a residue of formula V as hereinbefore defined.

Non-limiting examples of Compounds of Formula I include:

2-(3'-methoxycarbonyl-2'-methyl-prop-2'-yl)-4-methoxyphenol 2-(3'-n-hexyloxycarbonyl-2'-methyl-prop-2'-yl)-4-methoxyphenol 5-t-butyl-2-(3'-n-hexyloxycarbonyl-2'-methyl-prop-2'-yl)-4-methoxyphenol 5-t-butyl-2-(3'-n-dodecyloxycarbonyl-2'-methyl-prop-2'-yl)-4-methoxyphenol 2,5-bis-(3'-methoxycarbonyl-2'-methyl-prop-2'-yl)-4-methoxyphenol 2,5-bis-(3'-n-hexyloxycarbonyl-2'-methyl-prop-2'-yl)-4-methoxyphenol 2,5-bis-(3'-n-dodecyloxycarbonyl-2'-methyl-prop-2'-yl)-4-methoxyphenol 2-(4'-methoxycarbonyl-1'-methyl-cyclohex-1'-yl)-4-methoxyphenol 2-(4'-n-hexyloxycarbonyl-1'-methyl-cyclohex-1'-yl)-4-methoxyphenol 2,5-bis-(4'-methoxycarbonyl-1'-methyl-cyclohex-1'-yl)-4-methoxyphenol 2,5-bis-(4'-n-hexyloxycarbonyl-1'-methyl-cyclohex-1'-yl)-4-methoxyphenol 2,5-bis-(3',4'-bis-methoxycarbonyl-1'-methyl-cyclohex-1'-yl)-4-methoxyphenol 2 and 3-(3',4'-bis-methoxycarbonyl-cyclohex-1'-yl)-4-methoxyphenol 2 and 3-(4'-acetyl-1'-methyl-cyclohex-1'-yl)-4-methoxyphenol 2 and 3-(5'-methoxycarbonyl-2'-methyl-pent-2'-yl)-4-methoxyphenol 2-(5'-n-hexyloxycarbonyl-2'-methyl-pent-2'-yl)-4-methoxyphenol 2-(5'-n-hexyloxycarbonyl-2'-methyl-pent-2'-yl)-5-methyl-4-methoxyphenol 5-(5'-methoxycarbonyl-2'-methyl-pent-2'-yl)-2-methyl-4-methoxyphenol 5-(5'-n-hexyloxycarbonyl-2'-methyl-pent-2'-yl)-2-t-butyl-4-methoxyphenol 2-(5'-n-hexyloxycarbonyl-2'-methyl-pent-2'-yl)-5-t-butyl-4-methoxyphenol 5-(5'-n-hexyloxycarbonyl-2'-methyl-pent-2'-yl)-2-t-butyl-4-methoxyphenol 5-(5'-n-dodecyloxycarbonyl-2'-methyl-pent-2'-yl)-2-t-butyl-4-methoxyphenol 5-(5'-methoxycarbonyl-2'-methyl-pent-2'-yl)-2-(1',1',3',3'-tetramethylbutyl)-4-methoxyphenol 2-(5'-methoxycarbonyl-2'-methyl-pent-2'-yl)-5-(1',1',3',3'-tetramethylbutyl)-4-methoxyphenol 2,5-bis-(5'-methoxycarbonyl-2'-methyl-pent-2'-yl)-4-methoxyphenol 2,6-bis-(5'-methoxycarbonyl-2'-methyl-pent-2'-yl)-4-methoxyphenol 2,5-bis-(5'-ethoxycarbonyl-2'-methyl-pent-2'-yl)-4-methoxyphenol 2,5-bis-(5'-n-propyloxycarbonyl-2'-methyl-pent-2'-yl)-4-methoxyphenol 2-(5'-n-hexyloxycarbonyl-2'-methyl-pent-2'-yl)-5-(3'-n-hexyloxycarbonyl-2'-methyl-prop-2'-yl)-4-methoxyphenol 2-(5'-n-hexyloxycarbonyl-2'-methyl-pent-2'-yl)-5-(3'-n-octyloxycarbonyl-2'-methyl-prop-2'-yl)-4-methoxyphenol 2,5-bis-(5'-iso-propyloxycarbonyl-2'-methyl-pent-2'-yl)-4-methoxyphenol 2,5-bis-(5'-n-butyloxycarbonyl-2'-methyl-pent-2'-yl)-4-methoxyphenol 2,5-bis-(5'-iso-butyloxycarbonyl-2'-methyl-pent-2'-yl)-4-methoxyphenol 2,5-bis-(5'-n-pentyloxycarbonyl-2'-methyl-pent-2'-yl)-4-methoxyphenol 2,5-bis-(5'-iso-pentyloxycarbonyl-2'-methyl-pent-2'-yl)-4-methoxyphenol 2,5-bis-(5'-n-hexyloxycarbonyl-2'-methyl-pent-2'-yl)-4-methoxyphenol 2,5-bis-(5'-n-heptyloxycarbonyl-2'-methyl-pent-2'-yl)-4-methoxyphenol 2,5-bis-(5'-cyclohexyloxycarbonyl-2'-methyl-pent-2'-yl)-4-methoxyphenol 2,5-bis-(5'-n-octyloxycarbonyl-2'-methyl-pent-2'-yl)-4-methoxyphenol 2,5-bis-[5'-(2''-ethylhexyloxycarbonyl)-2'-methyl-pent-2'-yl]-4-methoxyphenol 2,5-bis-(5'-n-dodecyloxycarbonyl-2'-methyl-pent-2'-yl)-4-methoxyphenol 2,5-bis-(5'-n-hexadecyloxycarbonyl-2'-methyl-pent-2'-yl)-4-methoxyphenol 2,5-bis-[5'-(2''-methoxyethoxycarbonyl)-2'-methyl-pent-2'-yl]-4-methoxyhenol 2,5-bis-[5'-(2''-n-butyloxyethoxycarbonyl)-2'-methyl-pent-2'-yl]-4-methoxyphenol 2,5-bis-[5'-(2''-cyclohexyloxyethoxycarbonyl)-2'-methyl-pent-2'-yl]-4-methoxyphenol 2,5-bis-[5'-(2''-allyloxyethoxycarbonyl)-2'-methyl-pent-2'-yl]-4-methoxyphenol 2,5-bis-[5'-(2''-benzyloxyethoxycarbonyl)-2'-methyl-pent-2'-yl]-4-methoxyphenol 2,5-bis-[5'-(2''-phenoxyethoxycarbonyl)-2'-methyl-pent-2'-yl]-4-methoxyphenol 2,5-bis-(5'-phenoxycarbonyl-2'-methyl-pent-2'-yl)-4-methoxyphenol 2,5-bis-(5'-benzyloxycarbonyl-2'-methyl-pent-2'-yl)-4-methoxyphenol 2,5-bis-(5'-tetrahydrofurfuryloxycarbonyl-2'-methyl-pent-2'-yl)-4-methoxyphenol 2,5-bis-(5'-furfuryloxycarbonyl-2'-methyl-pent-2'-yl)-4-methoxyphenol 2,5-bis-[5'-(tetrahydrofuran-4-yloxycarbonyl)-2'-methyl-pent-2'-yl]-4-methoxyphenol 2-(5'-n-hexyloxycarbonyl-2'-methyl-pent-2'-yl)-5-(5'-methoxycarbonyl-2'-methyl-pent-2'-yl)-4-methoxyphenol
2,5-bis-(5'-carboxy-2'-methyl-pent-2'-yl)-4-methoxyphenol and its sodium salt
2,5-bis-(5'-methoxycarbonyl-2'-methyl-pent-2'-yl)-4-ethoxyphenol
2,5-bis-(5'-ethoxycarbonyl-2'-methyl-pent-2'-yl)-4-ethoxyphenol
2,5-bis-(5'-n-propyloxycarbonyl-2'-methyl-pent-2'-yl)-4-ethoxyphenol
2,5-bis-(5'-n-butoxycarbonyl-2'-methyl-pent-2'-yl)-4-ethoxyphenol
2-(5'-n-hexyloxycarbonyl-2'-methyl-pent-2'-yl)-5-(3'-n-hexyloxycarbonyl-2'-methyl-prop-2'-yl)-4-ethoxyphenol
2-(5'-n-hexyloxycarbonyl-2'-methyl-pent-2'-yl)-5-(3'-n-octyloxycarbonyl-2'-methyl-prop-2'-yl)-4-ethoxyphenol
2,5-bis-(5'-iso-propyloxycarbonyl-2'-methyl-pent-2'-yl)-4-ethoxyphenol
2,5-bis-(5'-n-butyloxycarbonyl-2'-methyl-pent-2'-yl)-4-ethoxyphenol
2,5-bis-(5'-iso-butyloxycarbonyl-2'-methyl-pent-2'-yl)-4-ethoxyphenol
2,5-bis-(5'-n-pentyloxycarbonyl-2'-methyl-pent-2'-yl)-4-ethoxyphenol
2,5-bis-(5'-iso-pentyloxycarbonyl-2'-methyl-pent-2'-yl)-4-ethoxyphenol
2,5-bis-(5'-n-hexyloxycarbonyl-2'-methyl-pent-2'-yl)-4-ethoxyphenol
2,5-bis-(5'-n-heptyloxycarbonyl-2'-methyl-pent-2'-yl)-4-ethoxyphenol
2,5-bis-(5'-cyclohexyloxycarbonyl-2'-methyl-pent-2'-yl)-4-ethoxyphenol
2,5-bis-(5'-n-octyloxycarbonyl-2'-methyl-pent-2'-yl)-4-ethoxyphenol
2,5-bis-[5'-(2''-ethylhexyloxycarbonyl)-2'-methyl-pent-2'-yl]-4-ethoxyphenol
2,5-bis-(5'-n-dodecyloxycarbonyl-2'-methyl-pent-2'-yl)-4-ethoxyphenol
2,5-bis-(5'-n-hexadecyloxycarbonyl-2'-methyl-pent-2'-yl)-4-ethoxyphenol
2,5-bis-[5'-(2''-methoxyethoxycarbonyl)-2'-methyl-pent-2'-yl]-4-ethoxyphenol
2,5-bis-[5'-(2''-n-butyloxyethoxycarbonyl)-2'-methyl-pent-2'-yl]-4-ethoxyphenol
2,5-bis-[5'-(2''-cyclohexyloxyethoxycarbonyl)-2'-methyl-pent-2'-yl]-4-ethoxyphenol
2,5-bis-[5'-(2''-allyloxyethoxycarbonyl)-2'-methyl-pent-2'-yl]-4-ethoxyphenol
2,5-bis-[5'-(2''-benzyloxyethoxycarbonyl)-2'-methyl-pent-2'-yl]-4-ethoxyphenol
2,5-bis-[5'-(2''-phenoxyethoxycarbonyl)-2'-methyl-pent-2'-yl]-4-ethoxyphenol
2,5-bis-(5'-phenoxycarbonyl-2'-methyl-pent-2'-yl)-4-ethoxyphenol
2,5-bis-(5'-benzyloxycarbonyl-2'-methyl-pent-2'-yl)-4-ethoxyphenol
2,5-bis-(5'-tetrahydrofurfuryloxycarbonyl-2'-methyl-pent-2'-yl)-4-ethoxyphenol
2,5-bis-(5'-furfuryloxycarbonyl-2'-methyl-pent-2'-yl)-4-ethoxyphenol
2,5-bis-[5'-(tetrahydropyran-4''-yloxycarbonyl)-2'-methyl-pent-2'-yl]-4-ethoxyphenol
2-(5'-n-hexyloxycarbonyl-2'-methyl-pent-2'-yl)-5-(5'-mehoxycarbonyl-2'-methyl-pent-2'-yl)-4-ethoxyphenol
2,5-bis-(5'-carboxy-2'-2'-methyl-pent-2'-yl)-4-ethoxyphenol and its sodium salt
2,5-bis-(2'-methyl-6'-hydroxy-hex-2'-yl)-4-ethoxyphenol
2,5-bis-(5'-methoxycarbonyl-2'-methyl-pent-2'-yl)-4-n-butoxyphenol
2,5-bis-(5'-ethoxycarbonyl-2'-methyl-pent-2'-yl)-4-n-butoxyphenol
2,5-bis-(5'-n-propyloxycarbonyl-2'-methyl-pent-2'-yl)-4-n-butoxyphenol
2-(5'-n-hexoxycarbonyl-2'-methyl-pent-2'-yl)-5-(3'-n-hexyloxycarbonyl-2'-methyl-prop-2'-yl)-4-n-butoxyphenol
2-(5'-n-hexyloxycarbonyl-2'-methyl-pent-2'-yl)-5-(3'-n-octyloxycarbonyl-2'-methyl-prop-2'-yl)-4-n-butoxyphenol
2,5-bis-(5'-iso-propyloxycarbonyl-2'-methyl-pent-2'-yl)-4-n-butoxyphenol
2,5-bis-(5'-n-butyloxycarbonyl-2'-methyl-pent-2'-yl)-4-n-butoxyphenol
2,5-bis-(5'-iso-butyloxycarbonyl-2'-methyl-pent-2'-yl)-4-n-butoxyphenol
2,5-bis-(5'-n-pentyloxycarbonyl-2'-methyl-pent-2'-yl)-4-n-butoxyphenol
2,5-bis-(5'-iso-pentyloxycarbonyl-2'-methyl-pent-2'-yl)-4-n-butoxyphenol
2,5-bis-(5'-n-hexyloxycarbonyl-2'-methyl-pent-2'-yl)-4-n-butoxyphenol
2,5-bis-(5'-n-heptyloxycarbonyl-2'-methyl-pent-2'-yl)-4-n-butoxyphenol
2,5-bis-(5'-cyclohexyloxycarbonyl-2'-methyl-pent-2'-yl)-4-n-butoxyphenol
2,5-bis-(5'-n-octyloxycarbonyl-2'-methyl-pent-2'-yl)-4-n-butoxyphenol
2,5-bis-[5'-(2''-ethylhexyloxycarbonyl)-2'-methyl-pent-2'-yl]-4-n-butoxyphenol
2,5-bis-(5'-n-dodecyloxycarbonyl-2'-methyl-pent-2'-yl)-4-n-butoxyphenol
2,5-bis-(5'-n-hexadecyloxycarbonyl-2'-methyl-pent-2'-yl)-4-n-butoxyphenol
2,5-bis-[5'-(2''-methoxyethoxycarbonyl)-2'-methyl-pent-2'-yl]-4-n-butoxyphenol
2,5-bis-[5'-(2''-n-butyloxyethoxycarbonyl)-2'-methyl-pent-2'-yl]-4-n-butoxyphenol
2,5-bis-[5'-(2''-cyclohexyloxyethoxycarbonyl)-2'-methyl-pent-2'-yl]-4-n-butoxyphenol
2,5-bis-[5'-(2''-allyloxyethoxycarbonyl)-2'-methyl-pent-2'-yl]-4-n-butoxyphenol
2,5-bis-[5'-(2''-benzyloxyethoxycarbonyl)-2'-methyl-pent-2'-yl]-4-n-butoxyphenol
2,5-bis-[5'-(2''-phenoxyethoxycarbonyl)-2'-methyl-pent-2'-yl]-4-n-butoxyphenol
2,5-bis-(5'-phenoxycarbonyl-2'-methyl-pent-2'-yl)-4-n-butoxyphenol
2,5-bis-(5'-benzyloxycarbonyl-2'-methyl-pent-2'-yl)-4-n-butoxyphenol
2,5-bis-(5'-tetrahydrofurfuryloxycarbonyl-2'-methyl-pent-2'-yl)-4-n-butoxyphenol
2,5-bis-(5'-furfuryloxycarbonyl-2'-methyl-pent-2'-yl)-4-n-butoxyphenol
2,5-Bis-[5'-(tetrahydropyran-4''-yloxycarbonyl)-2'-methyl-pent-2'-yl]-4-n-butoxyphenol
2-(5'-n-hexyloxycarbonyl-2'-methyl-pent-2'-yl)-5-(5'-methoxycarbonyl-2'-methyl-pent-2'-yl)-4-n-butoxyphenol
2,5-bis-(5'-carboxy-2'-methyl-pent-2'-yl)-4-n-butoxyphenol and its sodium salt 2,5-bis-(5'-methoxycarbonyl-2'-methyl-pent-2'-yl)-4-n-hexyloxyphenol
2,5-bis-(5'-methoxycarbonyl-2'-methyl-pent-2'-yl)-4-cyclohexyloxyphenol
2,5-bis-(5'-methoxycarbonyl-2'-methyl-pent-2'-yl)-4-(2'-n-butoxyethoxy)-phenol
2,5-bis-(5'-methoxycarbonyl-2'-methyl-pent-2'-yl)-4-(2'-ethylhexyloxy)-phenol
2,5-bis-(5'-methoxycarbonyl-2'-methyl-pent-2'-yl)-4-n-dodecyloxyphenol
2,5-bis-(5'-methoxycarbonyl-2'-methyl-pent-2'-yl)-4-n-hexadecyloxyphenol
2,5-bis-(5'-methoxycarbonyl-2'-methyl-pent-2'-yl)-4-benzyloxyphenol
2,5-bis-(5'-methoxycarbonyl-2'-methyl-pent-2'-yl)-4-phenoxyphenol
2,5-bis-(5'-cyano-2'-methyl-pent-2'-yl)-4-methoxyphenol
2,5-bis-(5'-carbamoyl-2'-methyl-pent-2'-yl)-4-methoxyphenol
2,5-bis-(5'-N-n-butylcarbamoyl-2'-methyl-pent-2'-yl)-4-methoxyphenol
2,5-bis-(5'-N-N-dimethylcarbamoyl-2'-methyl-pent-2'-yl)-4-methoxyphenol
2,5-bis-(5'-N-n-octylcarbamoyl-2'-methyl-pent-2'-yl)-4-methoxyphenol
2,5-bis-(5'-N,N-di-n-butylcarbamoyl-2'-methyl-pent-2'-yl)-4-methoxyphenol
2,5-bis-(5'-N-eicosylcarbamoyl-2'-methyl-pent-2'-yl)-4-methoxyphenol
2,5-bis-(5'-N-allylcarbamoyl-2'-methyl-pent-2'-yl)-4-methoxyphenol
2,5-bis-(5'-N-cyclohexylcarbamoyl-2'-methyl-pent-2'-yl)-4-methoxyphenol
2,5-bis-(5'-N-benzylcarbamoyl-2'-methyl-pent-2'-yl)-4-methoxyphenol
2,5-bis-(5'-N-phenylcarbamoyl-2'-methyl-pent-2'-yl)-4-methoxyphenol
2,5-bis-(5'-morpholinocarbamoyl-2'-methyl-pent-2'-yl)-4-methoxyphenol
2-(7'-methoxycarbonyl-2',2',4'-trimethyl-hept-4'-yl)-5-t-butyl-4-methoxyphenol
2-(1',7'-di-methoxycarbonyl-4'-methyl-hept-4'-yl)-4-methoxyphenol
2,5-bis-(2'-methyl-6'-hydroxy-hex-2'-yl)-4-methoxyphenol
2,5-bis-(2',6'-dimethyl-8'-hydroxy-oct-2'-yl)-4-methoxyphenol
2,5-bis-(8'-acetyloxy-2',6'-dimethyl-oct-2'-yl)-4-methoxyphenol
2,5-bis-(2',6'-dimethyl-8'-propionyloxy-oct-2'-yl)-4-methoxyphenol
2,5-bis-(8'-butyryloxy-2',6'-dimethyl-oct-2'-yl-4-methoxyphenol
2,5-bis-(2',6'-dimethyl-8'-hexanoyloxy-oct-2'-yl)-4-methoxyphenol
2-(5'-diethylphosphono-5'-ethoxycarbonyl-2'-methyl-pent-2'-yl)-4-methoxyphenol
2,5-bis-(5',5'-di-ethoxycarbonyl-2'-methyl-pent-2'-yl)-4-methoxyphenol
2,5-bis-(2',6'-dimethyl-8'-eicosanoyloxy-oct-2'-yl)-4-methoxyphenol
2,5-bis-(8'-crotonyloxy-2',6'-dimethyl-oct-2'-yl)-4-methoxyphenol
2,5-bis-(8'-benzoyloxy-2',6'-dimethyl-oct-2'-yl)-4-methoxyphenol
2,5-bis-(2',6'-dimethyl-8'-phenacetyloxy-oct-2'-yl)-4-methoxyphenol
2,5-bis-(8'-cyclohexylcarbonyloxy-2',6'-dimethyl-oct-2'-yl)-4-methoxyphenol
2,5-bis-(8'-methoxy-2',6'-dimethyl-oct-2'-yl)-4-methoxyphenol
2,5-bis-(8'-butoxy-2',6'-dimethyl-oct-2'-yl)-4-methoxyphenol
2,5-bis-(8'-pentadecyloxy-2',6'-dimethyl-oct-2'-yl)-4-methoxyphenol
2 and 3-(8'-amino-2',6'-dimethyl-oct-2'-yl)-4-methoxyphenol
2,5-bis-(6'-amino-2'-methyl-hept-2'-yl)-4-methoxyphenol and its hydrochloride
2,5-bis-(6'-N-methylamino-2'-methyl-hept-2'-yl)-4-methoxyphenol
2,5-bis-(6'-N,N-dimethylamino-2'-methyl-hept-2'-yl)-4-methoxyphenol
2,5-bis-(6'-N-ethylamino-2'-methyl-hept-2'-yl)-4-methoxyphenol
2,5-bis-(6'-N,N-diethylamino-2'-methyl-hept-2'-yl)-4-methoxyphenol
2,5-bis-(6'-N-n-butylamino-2'-methyl-hept-2'-yl)-4-methoxyphenol
2,5-bis-(6'-N,N-di-n-butylamino-2'-methyl-hept-2'-yl)-4-methoxyphenol
2,5-bis-(2'-methyl-6'-morpholino-hept-2'-yl)-4-methoxyphenol
2 and 3-(6'-acetamido-2'-methyl-hept-2'-yl)-4-methoxyphenol
2,5-bis-(6'-acetamido-2'-methyl-hept-2'-yl)-4-methoxyphenol
2,5-bis-(6'-hexanamido-2'-methyl-hept-2'-yl)-4-methoxyphenol
2,5-bis-(12'-amino-2',13'-dimethyl-tetradec-2'-yl)-4-methoxyphenol
2,5-bis-(12'-amino-3',13'-dimethyltetradec-3'-yl)-4-methoxyphenol
2,5-bis-(12'-acetamido-2',13'-dimethyl-tetradec-2'-yl)-4-methoxyphenol
2,5-bis-(12'-acetamido-3',13'-dimethyl-tetradec-3'-yl)-4-methoxyphenol
2-(2'-methyl-4'-phosphono-but-2'-yl)-4-methoxyphenol and its sodium salts
2-(2'-methyl-4'-dimethylphosphono-but-2'-yl)-4-methoxyphenol
2-(4'-diethylphosphono-2'-methyl-but-2'-yl)-4-methoxyphenol
2-(4'-di-n-butylphosphono-2'-methyl-but-2'-yl)-4-methoxyphenol
5-t-butyl-2-(2'-methyl-4'-dimethylphosphono-but-2'-yl)-4-methoxyphenol
5-(1',1',3',3'-tetramethylbutyl)-2-(2'methyl-4'-dimethylphosphono-but-2'-yl)-4-methoxyphenol
2,5-bis-(2'-methyl-4'-di-methylphosphono-but-2'-yl)-4-methoxyphenol
2,5-bis-(2'-methyl-4'-di-ethylphosphono-but-2'-yl)-4-methoxyphenol
2,5-bis-(2'-methyl-4'-di-n-propylphosphono-but-2'-yl)-4-methoxyphenol
2-(5'-n-hexyloxycarbonyl-2'-methyl-pent-2'-yl)-5-(2'-methyl-4'-diethylphosphono-but-2'-yl)-4-methoxyphenol
2,5-bis-(2'-methyl-4'-di-iso-propylphosphono-but-2'-yl)-4-methoxyphenol
2,5-bis-(2'-methyl-4'-di-n-butyl-phosphono-but-2'-yl)-4-methoxyphenol
2,5-bis-[2'-methyl-4'-(di-2''-ethylhexyl-phosphono)-but-2'-yl]-4-methoxyphenol 2,5-bis-(2'-methyl-4'-di-n-dodecylphosphono-but-2'-yl)-4-methoxyphenol
2,5-bis-[2'-methyl-4'-(2''-oxo-1'',3'',2''-dioxaphospholan-2''-yl)-but-2'-yl]-4-methoxyphenol
2,5-bis-[2'-methyl-4'-(4''-methyl-2''-oxo-1'',3'',2''-dioxaphospholan-2''-yl)-but-2'-yl]-4-methoxyphenol
2,5-bis-[4'-(ethyl-ethylphosphino)-2'-methyl-but-2'-yl]-4-methoxyphenol
2,5-bis-(5'-ethoxycarbonyl-5'-diethylphosphono-2'-methyl-pent-2'-yl)-4-methoxyphenol
2,5-bis-(2'-methyl-3'-sulpho-prop-2'-yl)-4-methoxyphenol
2-(2'-methyl-3'-sulphonamido-prop-2'-yl)-4-methoxyphenol
5-t-butyl-2-(2'-methyl-3'-sulphonamido-prop-2'-yl)-4-methoxyphenol
2-(2'-methyl-3'-N-methylsulphonamido-prop-2'-yl)-4-methoxyphenol
5-(1',1',3',3'-tetramethylbutyl)-2-(2'-methyl-3'-N-methylsulphonamido-prop-2'-yl)-4-methoxyphenol
2-(2'-methyl-3'-N,N-di-n-butylsulphonamido-prop-2'-yl)-4-methoxyphenol
2-(2'-methyl-3'-N-n-octylsulphonamido-prop-2'-yl)-4-methoxyphenol
5-t-butyl-2-(2'-methyl-3'-N-n-octylsulfonamido-prop-2'-yl)-4-methoxyphenol
2-(7'-cyano-2',6'-dimethyl-hept-2'-yl)-4-methoxyphenol
2-(5'-methoxycarbonyl-2'-methyl-pent-2'-yl)-1,4-dimethoxybenzene
2-(5'-n-hexyloxycarbonyl-2'-methyl-pent-2'yl)-1,4-dimethoxybenzene
2-methyl-5-(5'-methoxycarbonyl-2'-methyl-pent-2'-yl)-1,4-dimethoxybenzene
2-t-butyl-5-(5'-methoxycarbonyl-2'-methyl-pent-2'-yl)-1,4-dimethoxybenzene
2-(5'-methoxycarbonyl-2'-methyl-pent-2'-yl)-5-(1',1',3',3'-tetramethylbutyl)-1,4-dimethoxybenzene
2,5-bis-(5'-methoxycarbonyl-2'-methyl-pent-2'-yl)-1,4-dimethoxybenzene
2,5-bis-(5'-ethoxycarbonyl-2'-methyl-pent-2'-yl)-1,4-dimethoxybenzene
2,5-bis-(5'-n-propyloxycarbonyl-2'-methyl-pent-2'-yl)-1,4dimethoxybenzene
2,5-bis-(5'-iso-propyloxycarbonyl-2'-methyl-pent-2'-yl)-1,4-dimethoxybenzene
2,5-bis-(5'-n-butoxycarbonyl-2'-methyl-pent-2'yl)-1,4-dimethoxybenzene
2,5-bis-(5'-n-hexyloxycarbonyl-2'-methyl-pent-2'-yl)-1,4-dimethoxybenzene
2,5-bis-(5'-(2''-ethylhexyloxycarbonyl)-2'-methyl-pent-2'-yl)-1,4-dimethoxybenzene
2,5-bis-(5'-n-butoxyethoxycarbonyl-2'-methyl-pent-2'-yl)-1,4-dimethoxybenzene
2,5-bis-(5'-tetrahydrofurfuryoxycarbonyl-2'-methyl-pent-2'-yl)-1,4-dimethoxybenzene
2,5-bis-(5'-carboxy-2'-methyl-pent-2'-yl)-1,4-dimethoxybenzene
2,5-bis-(4'-keto-2'-methyl-pent-2'-yl)-1,4-dimethoxybenzene
2-(5'-methoxycarbonyl-2'-methyl-pent-2'-yl)-1,4-diethoxybenzene
2-(5'-n-hexyloxycarbonyl-2'-methyl-pent-2'-yl)-1,4-diethoxybenzene
2-methyl-5-(5'-methoxycarbonyl-2'-methyl-pent-2'-yl)-1,4-diethoxybenzene
2-t-butyl-5-(5'-methoxycarbonyl-2'-methyl-pent-2'-yl)-1,4-diethoxybenzene
2-(5'-methoxycarbonyl-2'-methyl-pent-2'-yl)-5-(1',1',3',3'-tetramethylbutyl)-1,4-diethoxybenzene
2,5-bis-(5'-methoxycarbonyl-2'-methyl-pent-2'-yl)-1,4-diethoxybenzene
2,5-bis-(5'-ethoxycarbonyl-2'-methyl-pent-2'-yl)-1,4-diethoxybenzene
2,5-bis-(5'-n-propyloxycarbonyl-2'-methyl-pent-2'-yl)-1,4-diethoxybenzene
2,5-bis-(5'-iso-propyloxycarbonyl-2'-methyl-pent-2'-yl)-1,4-diethoxybenzene
2,5-bis-(5'-n-butoxycarbonyl-2'-methyl-pent-2'-yl)-1,4-diethoxybenzene
2,5-bis-(5'-n-hexyloxycarbonyl-2'-methyl-pent-2'-yl)-1,4-diethoxybenzene
2,5-bis-[5'-(2''-ethylhexyloxycarbonyl)-2'-methyl-pent-2'-yl]-1,4-diethoxybenzene
2,5-bis-(5'-n-butoxyethoxycarbonyl)-2'-methyl-pent-2'-yl)-1,4-diethoxybenzene
2,5-bis-(5'-tetrahydrofurfuryloxycarbonyl)-2'-methyl-pent-2'-yl)-1,4-diethoxybenzene
2,5-bis-(5'-carboxy-2'-methyl-pent-2'-yl)-1,4-diethoxybenzene
1-ethoxy-4-methoxy-2-(5'-methoxycarbonyl-2'-methyl-pent-2'-yl)-benzene
4-ethoxy-1-methoxy-2-(5'-methoxycarbonyl)-2'-methyl-pent-2'-yl)-benzene
2-t-butyl-1-ethoxy-4-methoxy-5-(5'-methoxycarbonyl-2'-methyl-pent-2'-yl)-benzene
2-t-butyl-4-ethoxy-1-methoxy-5-(5'-methoxycarbonyl-2'-methyl-pent-2'-yl)-benzene
1-ethoxy-4-methoxy-5-(5'-methoxycarbonyl-2'-methyl-pent-2'-yl)-2-(1',1',3',3'-tetramethylbutyl)-benzene
4-ethoxy-1-methoxy-5-(5'-methoxycarbonyl-2'-methyl-pent-2'-yl)-2-(1',1',3',3'-tetramethylbutyl)-benzene
1-ethoxy-4-methoxy-2,5-bis-(5'-methoxycarbonyl-2'-methyl-pent-2'-yl)-benzene
1-ethoxy-4-methoxy-2,5-bis-(5'-ethoxycarbonyl-2'-methyl-pent-2'-yl)-benzene
1-ethoxy-4-methoxy-2,5-bis-(5'-n-hexyloxycarbonyl-2'-methyl-pent-2'-yl)-benzene
1-ethoxy-4-methoxy-2,5-bis-(5'-n-butoxyethoxycarbonyl-2'-methyl-pent-2'-yl)-benzene
1-ethoxy-4-methoxy-2,5-bis-(5'-tetrahydrofurfuryloxycarbonyl-2'-methyl-pent-2'-yl)-benzene
1-ethoxy-4-methoxy-2,5-bis-(5'-carboxy-2'-methyl-pent-2'-yl)-benzene
5-hydroxy-6-(5'-methoxycarbonyl-2'-methyl-pent-2'-yl)-2,2-dimethylcoumaran
5-hydroxy-6-(5'-n-hexyloxycarbonyl-2'-methyl-pent-2'-yl)-2,2-dimethylcoumaran
6-hydroxy-7-(5'-methoxycarbonyl-2'-methyl-pent-2'-yl)-2,2-dimethylchroman
6-hydroxy-7-(5'-n-hexyloxycarbonyl-2'-methyl-pent-2'-yl)-2,2-dimethylchroman
6-hydroxy-7-(5'-methoxycarbonyl-2'-methyl-pent-2'-yl)-2,2,4-trimethyl-chroman
6-hydroxy-7-(5'-n-hexyloxycarbonyl-2'-methyl-pent-2'-yl)-2,2,4-trimethyl-chroman
6-hydroxy-7-(5'-methoxycarbonyl-2'-methyl-pent-2'-yl)-2,2-dimethyl-4-isopropyl-chroman
6-hydroxy-7-(5'-n-hexyloxycarbonyl-2'-methyl-pent-2'-yl)-2,2-dimethyl-4-isopropyl-chroman
6-hydroxy-7-(5'-methoxycarbonyl-2'-methyl-pent-2'-yl)-2-methyl-2-(4',8',12'-trimethyl-tridec-1'-yl)-chroman
bis-[5-hydroxy-2-methoxy-4-(5'-methoxycarbonyl-2'-methyl-pent-2'-yl)-phenyl]-methane bis-[5-hydroxy-2-methoxy-4-(5′-n-hexyloxycarbonyl-2′-methyl-2′-yl)-phenyl]-methane bis-[2-hydroxy-5-methoxy-3-(5′-methoxycarbonyl-2′-methyl-pent-2′-yl)-phenyl]-methane bis-2,2-[2-hydroxy-5-methoxy-4-(5′-methoxycarbonyl-2′-methyl-pent-2′-yl)-phenyl]-propane bis-2,2-[2-hydroxy-5-methoxy-4-(5′-n-hexyloxycarbonyl-2′-methyl-pent-2′-yl)-phenyl]-propane bis-[4-hydroxy-2,5-bis-(5′-methoxycarbonyl-2′-methyl-pent-2′-yl)-phenyl]-oxide 6-hydroxy-2-[2,5-dihydroxy-4-(5′-methoxycarbonyl-2′-methyl-pent-2′-yl)-phenyl]-7-(5′-methoxycarbonyl-2′-methyl-pent-2′-yl)-2,4,4-trimethyl-chroman 6,6′-dihydroxy-7,7′-bis-(5″-methoxycarbonyl-2″-methyl-pent-2″-yl-4,4,4′,4′-tetramethyl-2,2′-spiro-bis-chroman 5-(5′-n-hexyloxycarbonyl-2′-methyl-pent-2′-yl)-2-cumyl-4-methoxyphenol bis-[5-(2′-hydroxy-5′-methoxy-phenyl)-5-methyl-hexanoic acid]ester of hexane 1,6-diol N,N′-[5-(2′-hydroxy-5′-methoxy-phenyl)-5-methyl-hexanoic acid]amide of hexane-1,6-diamine.

Other non-limiting examples of compounds of formula I viz. those wherein $R_o$ is a group of formula IVa or IVb, as hereinbefore defined, are those having the formula:

[J]—(CH$_2$)$_4$—[J]

[J]—CH$_2$—CO—O—(CH$_2$)$_2$—O—CO—CH$_2$—[J]

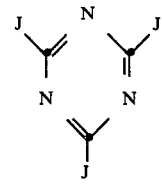

H$_{25}$C$_{12}$—CH—COOCH$_3$
            |
            J wherein J is a residue having the formula:

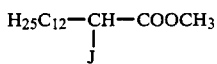

C(CH$_3$)$_2$—CH$_2$CH$_2$CH$_2$COOC$_2$H$_5$.

Non limiting examples of compounds of formula XIV (page 34) are

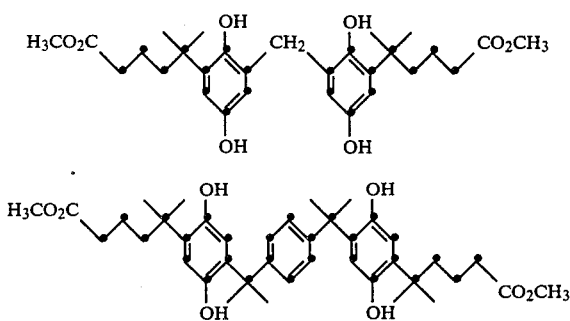

The present invention also provides a process for the production of compounds of formula I comprising reacting, in the presence of an acidic catalyst, a compound of formula X

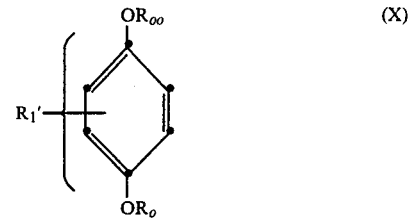

wherein $R_1'$ is hydrogen, a $C_{1-8}$ straight or branched chain alkyl group, or $C_7$-$C_9$ aralkyl, and $R_o$ and $R_{oo}$ have their previous significance, or $R_1'$ and $R_o$ together may form a residue of formula V as hereinbefore defined, with an alkylating agent capable of introducing one or two residues of formula II, as hereinbefore defined, or one residue of formula IX as hereinbefore defined, into either one or two aromatic rings of the compound of formula X.

The alkylation step is conveniently carried out at a temperature ranging from 20° C. to 150° C., but preferably in the range 20° C. to 100° C. The acid catalyst may be a Brönsted or Lewis acid or active earth. Brönsted acids suitable for the purpose may be organic or inorganic or a partial salt thereof and may be an inorganic acid such as hydrochloric, sulphuric, perchloric and orthophosphoric acid; an alkyl, aryl or alkaryl substituted inorganic acid such as methane and ethane sulphonic acids, benzene sulphonic acid, p-toluene sulphonic acid and methane phosphonic acid; an organic acid such as dichloroacetic acid, trichloroacetic acid, and trifluoroacetic acids. Lewis acids suitable for alkylation include boron trifluoride, ferric chloride, aluminium chloride and stannic chloride. Active earths suitable for alkylation include Fulmont 237 ® and Fulcat 22 ®.

The above-described catalysts may be used alone or in conjunction with a solvent or solvent mixture. Suitable solvents include ether, water, methanol, acetic acid, benzene and nitromethane. The preferred catalysts are sulphuric acid containing methanol, p-toluene sulphonic acid and aluminium chloride in combination with nitromethane solvent.

More specifically, compounds of formula I wherein q is 0 or 1 and p is 1 or 2 may be produced by reacting, in the presence of an acidic catalyst, 1 mole of a compound of formula X wherein $R_o$ and $R_{oo}$ each have their previous significance viz. a compound having the formula X as hereinbefore defined wherein $R_o$ and $R_{oo}$ have their previous singificance and $R_1'$ is as hereinbefore defined with from 0.1 to at least 2.0 moles of an alkylating agent capable of introducing the residue II into at least one aromatic ring of the compound of formula X.

Compounds of formula I wherein p is 1 and q is 1 may be produced by reacting, in the presence of an acidic catalyst, 1 mole of a compound of formula XI:

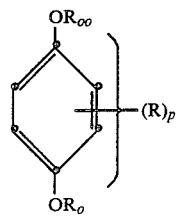
(XI)

wherein p is 1, R is a residue of formula II and $R_o$ and $R_{oo}$ have their previous significance, with at least 1.0 mole of an alkylating agent capable of introducing the residue II or IX into the ring of the compound of formula XI.

Compounds of formula IC

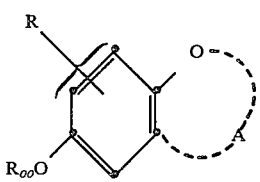
(IC)

where A is a carbon residue containing 4 to 20 carbon atoms which form a substituted chroman or coumaran system, and R and $R_{oo}$ are as previously defined, may be produced by reacting in the presence of an acid catalyst, 1 mole of a compound of formula (XA)

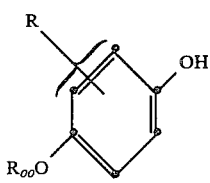
(XA)

where R and $R_{oo}$ are as previously defined, with at least 1 mole of an alkylating agent capable of introducing the residue A into the ring of the compound of formula (XA).

Alkylating agents which are suitable for this purpose have two reactive centres, and may be dienes, diols, hydroxy olefins, or halo olefins, such as isoprene, 2-methyl-penta-2,4-diene, 2-methyl-hexa-2,4-diene, 2,5-dimethyl-hexa-2,4-diene, methallyl alcohol, methallyl chloride, prenyl alcohol, phytol, 2-methyl-pentan-2,4-diol, 2,5-dimethyl-hexan-2,5-diol.

Compounds of formula Id

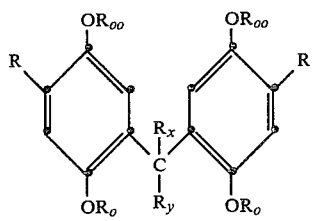
(Id)

where $R_x$ and $R_y$ are the same or different and are H or $C_1$-$C_4$ alkyl, and R, $R_o$ and $R_{oo}$ are as previously defined, may be prepared by reacting in the presence of an acid catalyst, 1 mole of a compound of formula XIA

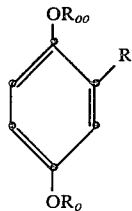
(XIA)

where R, $R_o$ and $R_{oo}$ are as previously defined, with up to 0.5 moles of an aldehyde or ketone having 1-9 carbon atoms.

Compounds of formula Ie

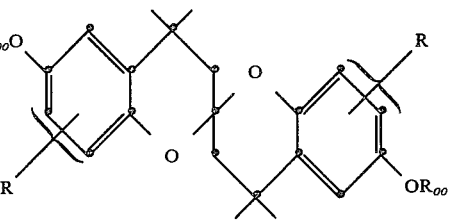
(Ie)

where R and $R_{oo}$ are as previously defined, may be prepared by reacting in the presence of an acid catalyst, 1 mole of a compound of formula XA with at least 1.5 moles of acetone or with up to 0.5 moles of phorone.

Compounds of formula If

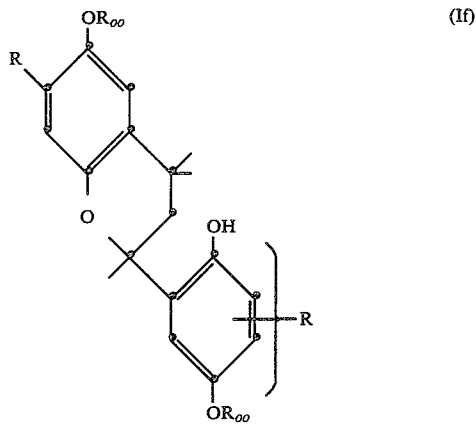
(If)

where R and $R_{oo}$ are as previously defined, may be prepared by reacting, in the presence of an acid, 1 mole of a compound of formula XA with at least 1 mole of acetone or with up to 0.5 moles of mesityl oxide.

In a further process, the compounds of formula I wherein $R_1$ is $C_1$-$C_8$ alkyl, $C_7$-$C_9$ aralkyl or a residue of formula II or III, one of $R_o$ and $R_{oo}$ is hydrogen and the other $R_o$ or $R_{oo}$ is a $C_1$-$C_{20}$ straight or branched alkyl optionally interrupted by 1 to 5 oxygen atoms, a $C_3$-$C_{12}$ cycloalkyl group, a $C_6$-$C_{10}$ aryl group or a $C_7$-$C_{13}$ aralkyl group and R has its previous significance, may be produced by reacting a compound of formula XII

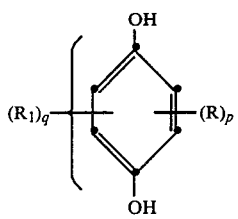 (XII)

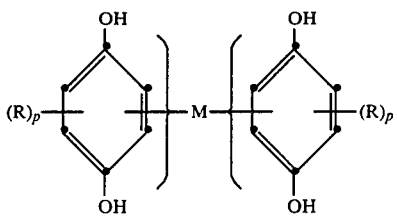 (XIV)

in the presence of a quinone, preferably the corresponding quinone analogue of formula XIII:

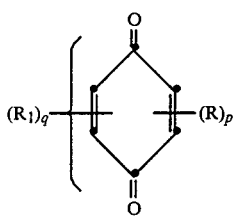 (XIII)

wherein in formula XII and XIII $R_1$ is $C_{1-8}$alkyl, $C_{7-9}$ aralkyl or a residue of formula II or III and R, p and q have their previous significance, with a compound having the formula $R_o$—OH or $R_{oo}$—OH wherein $R_o$ and $R_{oo}$ are the same or different and are a $C_1$-$C_{20}$ straight or branched alkyl group optionally interrupted by 1 to 5 oxygen atoms, a $C_3$-$C_{12}$cycloalkyl group, a $C_6$-$C_{10}$ aryl group or a $C_7$-$C_{13}$aralkyl group in an acidic medium. Further details of this process are described in GB Patent No. 1557237.

In a further process according to the invention, compounds of formula I wherein one of $R_o$ and $R_{oo}$ is hydrogen are produced by reacting the quinone analogues of formula XIII with a compound of formula $(R_oO)_3P$ or $(R_{oo}O)_3P$, wherein $R_o$ and $R_{oo}$ are the same or different and are a $C_1$-$C_{20}$ straight or branched alkyl group optionally interrupted by 1 to 5 oxygen atoms, a $C_3$-$C_{12}$ cycloalkyl group, a $C_6$-$C_{10}$ aryl group atoms or a $C_7$-$C_{13}$ aralkyl group and then hydrolysing the resulting phosphate using the method described by F. Ramirez et al. J. Am. Chem. Soc. 81, 4338, 1959.

In a still further process, compounds of formula I wherein each of $R_o$ and $R_{oo}$ is other than hydrogen may be produced by reacting a compound of formula I wherein $R_o$ and $R_{oo}$ are each hydrogen, or one is hydrogen, with a compound $R_o$—OH (or $R_{oo}$—OH) in an acidic medium or with a compound $R_o$—X or $R_{oo}$—X) or $(R_o)_2SO_4$ or $(R_{oo})_2SO_4$, in an alkaline medium, wherein $R_o$ and $R_{oo}$ are the same or different and are a $C_1$-$C_{20}$ straight or branched alkyl group optionally interrupted by 1 to 5 oxygen atoms, a $C_3$-$C_{12}$ cycloalkyl group, a $C_6$-$C_{10}$ aryl group or a $C_7$-$C_{13}$ aralkyl group and X is halogen.

Compounds of formula XII wherein $R_1$ is $C_7$-$C_9$aralkyl are new compounds. Compounds of formula XII may be prepared by reacting, in the presence of an acid catalyst, a hydroquinone of formula X ($R_o$ and $R_{oo}$ both being hydrogen and $R_1'$ is hydrogen or $C_1$-$C_8$ alkyl or $C_7$-$C_9$aralkyl) with a functional alkylating agent capable of introducing p moles of a group R, as hereinbefore defined. Examples of suitable functional alkylating agents are set out hereinafter.

Compounds of formula XII which contain a residue of formula III are also novel and have the formula XIV in which R, M and p have their previous significance. Compounds of formula XIV are active as stabilisers for magenta couplers.

Compounds of formula XIV may be produced by methods well known per se e.g. by condensing 2 moles of a compound of formula XII where q=0 with an agent capable of introducing the linkage —M—.

Compounds XIII are also new compounds and may be produced by oxidising the compounds of formula XII. Examples of suitable oxidising agents are salts of an element capable of abstracting electrons and possessing a suitable redox potential; a hypohalite; a perhalate; nitric acid; an oxide of nitrogen; chromium trioxide, a chromate, Jones' reagent, an organic oxidising agent; oxygen or air, optionally catalysed by metal salts.

The preparation of compounds of formula I wherein $R_o$ is a group of formula IVa or IVb, as hereinbefore defined, may be effected by reacting either 2 or 3 moles of a compound of formula XII A:

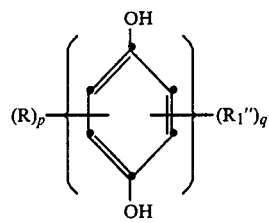 (XIIA)

wherein R, $R_1''$, p and q have their previous significance, in the presence of a base, with a corresponding di- or tri-halide Hal—B(Hal)$_m$, epichlorohydrin, epibromohydrin, or a diglycidyl ether compound

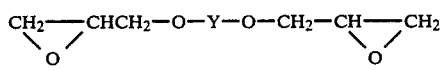

respectively; or by reacting a compoun of formula XIIA, in the presence of a base, with a halide

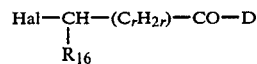

wherein m, r, B, R, $R_{16}$ and D have their previous significance and Hal represents chlorine and, especially, bromine.

The compounds of formula XII A may be prepared in the manner previously described for the production of compounds of formula XII, by reacting, in the presence of an acid catalyst, a compound of formula X wherein $R_o$ and $R_{oo}$ are each hydrogen, with a functional alkylating agent capable of introducing one or two residues of formula II as hereinbefore defined.

Non limiting examples of compound of formula X include:

hydroquinone-monomethyl ether
hydroquinone-monoethyl ether
hydroquinone-mono-n-propyl ether
hydroquinone-mono-iso-propyl ether
hydroquinone-mono-n-butyl ether
hydroquinone-mono-sec-butyl ether
hydroquinone-mono-n-pentyl ether
hydroquinone-mono-n-hexyl ether
hydroquinone-mono-n-octyl ether
hydroquinone-mono-2-ethylhexyl ether
hydroquinone-mono-dodecyl ether
hydroquinone-mono-hexadecyl ether
hydroquinone-mono-cyclohexyl ether
hydroquinone-mono-n-butoxyethyl ether
hydroquinone-mono-benzyl ether
hydroquinone-mono-phenyl ether
2-methyl-4-methoxyphenol
2-ethyl-4-methoxyphenol
2-iso-propyl-4-methoxyphenol
2-t-butyl-4-methoxyphenol
2-(1',1',3',3'-tetramethylbutyl)-4-methoxyphenol
1,4-dimethoxybenzene
2-methyl-1,4-dimethoxybenzene
2-t-butyl-1,4-dimethoxybenzene
1,4-diethoxybenzene
2-methyl-1,4-diethoxybenzene
2-t-butyl-1,4-diethoxybenzene
1,4-di-n-propoxybenzene
1,4-di-n-butoxybenzene
2-t-butyl-1-ethoxy-4-methoxybenzene Functional alkylating agents capable of introducing a residue a formula II which are reacted with the hydroquinone contain a reactive centre, for example, an olefinic or hydroxy group which is eliminated, transformed or rearranged during the course of the alkylation reaction.

Examples of functional olefins suitable for the functional alkylation of compounds of formula X,XA and XI are:
5-methylhex-5-enoic acid
methyl 5-methylhex-5-enoate
ethyl 5-methylhex-5-enoate
n-propyl 5-methylhex-5-enoate
iso-propyl 5-methylhex-5-enoate
n-butyl 5-methylhex-5-enoate
iso-butyl 5-methylhex-5-enoate
sec-butyl 5-methylhex-5-enoate
n-pentyl 5-methylhex-5-enoate
iso-pentyl 5-methylhex-5-enoate
sec-pentyl 5-methylhex-5-enoate
n-hexyl 5-methylhex-5-enoate
cyclohexyl 5-methylhex-5-enoate
2-ethylhexyl 5-methylhex-5-enoate
n-octyl 5-methylhex-5-enoate
n-dodecyl 5-methylhex-5-enoate
n-hexadecyl 5-methylhex-5-enoate
methyl 5,7,7-trimethyl-oct-4-enoate
1,7-di-methoxycarbonyl-4-methyl-hept-3-ene
4-carbomethoxy-1-methylcyclohex-1-ene
4-acetyl-1-methylcyclohex-1-ene
4,5-bis-carbomethoxy-1-methylcyclohex-1-ene
dimethylprenylphosphonate
diethylprenylphosphonate
dipropylprenylphosphonate
di-isopropylprenylphosphonate
di-n-butylprenylphosphonate
di-n-octylprenylphosphonate
citronellol
citronellyl acetate
citronellyl methyl ether
citronellyl butyl ether
2-amino-6-methyl-hept-5-ene
2-amino-6-methyl-hept-6-ene
diethyl 2-ethoxycarbonyl-5-methyl-hex-4-ene-2-phosphonate
ethyl 2-ethoxycarbonyl-5-methyl-hex-4-enoate
citronellyl nitrile
2-acetamido-6-methyl-hept-5-ene
2-acetamido-6-methyl-hept-6-ene
2-methyl-2-propene-1-sulphonic acid
2-methyl-2-propene-1-sulphonic acid amide
N-n-butyl-2-propene-1-sulphonic acid amide
N,N-di-n-butyl-2-propene-sulfphonic acid amide
N-n-octyl-2-propene-1-sulfphonic acid amide Examples of functional hydroxy compounds suitable for the functional alkylation of compounds of formula X, XA and XI are
2-amino-6-hydroxy-6-methylheptane
2-acetamido-6-hydroxy-6-methylheptane
11-amino-2,2,12-trimethyl-tridecan-1-ol
as well as members selected from 11-amino-undecanols of the formula:

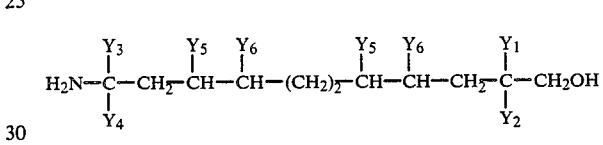

wherein $Y_1$ and $Y_3$, independently, are —H or $C_1$–$C_8$ alkyl; $Y_2$ and $Y_4$, independently, are $C_1$–$C_8$ alkyl; and $Y_5$ and $Y_6$, independently, are —H or $C_1$–$C_4$ alkyl.

These 11-amino-undecanols are described in more detail, together with their method of manufacture in German Offenlegungsschrift No. 2831299.

Examples of olefins suitable of the alkylation of compounds of formula XI wherein p is 1, $R_1$, $R_o$ and $R_{oo}$ have their previous significance and R is a residue of formula II are isobutylene, diisobutylene and α-methyl styrene. Examples of alcohols suitable for the alkylation of compounds of formula XI wherein p is 1 and $R_1$, $R_o$ and $R_{oo}$ have their previous significance are t-butanol, 1,1,3,3-tetramethyl-butan-1-ol and cumyl alcohol.

Any functional derivative of a compound of formula I may be converted to a different functional derivative. For example when Q is the acid group —$CO_2H$ it may be esterified with an alcohol $R_4OH$ to give the corresponding ester —$CO_2R_4$, or when Q is the ester group —$CO_2R_4$ it may be transesterified to give a different $R_4$ group, or alternatively the ester group —$CO_2R_4$ may be converted to an amide —$CON(R_4)(R_5)$ by treatment with $NH(R_4)(R_5)$, wherein $R_4$ and $R_5$ have their previous significance.

The compounds of formula I provide a valuable means of introducing a wide variety of functional residues for optimal photographic effect. For example, the polarity of and/or ballast in hydroquinone ethers of formula I are able to be regulated, and hence provide an effective control of solubility, compatibility, mobility-/immobility for photographic systems. Such qualities make the compounds of formula I valuable intermediates for the preparation of more complex photographically useful compounds and render them useful as photographic stabilisers. A particularly advantageous property exhibited by the compounds of formula I, when used as photographic stabilisers, is that they do not have a deleterious effect on the dye yield, in contrast with previously-known substituted hydroquinones which reduce dye yield.

The compounds of the formula (I) as well as colour couplers can be incorporated in a known manner in photographic layers, for example in silver halide emulsions containing gelatin and/or other binders. For example, they can be used in silver bromide, silver chloride or silver iodide emulsions or in those emulsions which contain a mixture of silver halides, such as silver bromide/iodide or silver chloride/bromide emulsions.

The emulsions can be chemically sensitised and they can also contain further known organic stabilisers, such as hindered amines, phenolic compounds such as hindered phenols, alkoxyphenols, aryloxyphenols, hydroxycoumarans, hydroxychromans or dihydroxyspirochromans, or hydroquinones and especially hydroquinones of formula XII, whereby synergistic effects may be achieved, and UV absorbers, optical brightening agents and photographically active compounds such as antifogging agents or compounds which release a photographically active chemical such as DIR compounds, as well as customary plasticisers, for example glycerine. The emulsions can also be hardened with the hardeners customary for gelatin, furthermore the emulsions can contain customary coating assistants.

The emulsions can be applied to layer supports customary for photographic recording material. Optionally, a mixture of several colloids can be used to disperse the silver halides. The emulsions can also contain couplers, either alone or as a mixture, producing dyes during development, e.g. yellow, magenta, cyan or black dyes.

The customary developer baths can be employed for developing the recording material for colour photography. These baths as a rule contain a developer substance of the p-phenylenediamine type, a development retarder, such as potassium bromide, an antioxidant, such as sodium sulfite, a salt of sulfurous acid and/or hydroxylamine, and a base for example an alkali metal hydroxide or alkali metal carbonate. Furthermore, the developer baths can contain a conventional antifogging agent, complexing agents, wetting agents, optical brightening agents and others.

Corresponding application possibilities are described, for example, in U.S. Pat. Nos. 2,304,939, 2,304,940, 2,322,027, 2,284,879, 2,801,170, 2,801,171, 2,749,360 and 2,825,382.

The following Examples further illustrate the present invention. Parts and percentages shown therein are by weight.

EXAMPLE 1

(a) 100 parts of 98% sulphuric acid are added to 32 parts of methanol keeping the temperature below 10° C. To this solution is then added 35.5 parts of methyl 5-methyl-hex-5-enoate followed by 12.4 parts of hydroquinone monomethyl ether. After stirring for 24 hours at room temperature the reaction mixture is poured into water, and the oil which separated extracted with ether. The ether extract after washing with 2N sodium hydroxide solution and then water is evaporated. Dilution of this oil with 40°–60° petroleum ether containing a little ether gives 2,5-bis-(5'-methoxycarbonyl-2'-methyl-pent-2'-yl)-4-methoxyphenol m.p. 82°–4° C. with the following percentage composition by weight.

|  | Carbon | Hydrogen |
|---|---|---|
| Found | 67.99 | 9.16 |
| Calculated for $C_{23}H_{36}O_6$ | 67.62 | 8.88 |

(b) The sodium hydroxide washings from the above ether extract are heated on a steam-bath for 2 hours and then acidified. The solid obtained is filtered off, washed with water, and then crystallised from glacial acetic acid-water to give 2,5-bis-(5'-carboxy-2'-methylpent-2'-yl)-4-methoxyphenol with m.p. 177°–9° C. and the following percentage composition by weight.

|  | Carbon | Hydrogen |
|---|---|---|
| Found | 65.80 | 8.31 |
| Calculated for $C_{21}H_{32}O_6$ | 66.29 | 8.48 |

EXAMPLE 2a

110 Parts of hydroquinone, 284 parts of methyl 5-methyl-hex-5-enoate, and 10 parts of p-toluene sulphonic acid are heated on a stream-bath for 24 hours. The cooled reaction mixture partially solidified and after trituration with ether, yields after filtration, 2,5-bis-(5'-methoxycarbonyl-2'-methyl-pent-2'-yl)-hydroquinone, m.p. 150°–3° C. After crystallisation from ethanol/water, the product has m.p. of 160°–2° C. with the following percentage composition by weight.

|  | Carbon | Hydrogen |
|---|---|---|
| Found | 67.05 | 8.96 |
| Calculated for $C_{22}H_{34}O_6$ | 66.98 | 8.69 |

EXAMPLE 2b

44 Parts of 2,5-bis-(5'-carboxy-2'-methyl-pent-2'-yl)-hydroquinone are added in portions to 375 parts of 10–14% w/v aqueous sodium hypochlorite solution with vigorous stirring, the temperature being maintained between 25°–30° C. with a cold water bath. The mixture is stirred at room temperature for 1 hour, diluted with 300 parts of water, and acidified with concentrated hydrochloric acid to give, after filtration, 2,5-bis-(5'-carboxy-2'-methyl-pent-2'-yl)-1,4-benzoquinone. After crystallisation from methanol the product has a m.p. of 204°–6° C. From methyl alcohol and 2,5-bis-(5'-carboxy-2'-methylpent-2'-yl)-1,4-benzoquinone using hydrogen chloride as a catalyst is prepared 2,5-bis-(5'-methoxycarbonyl-2'-methyl-pent-2'-yl)-1,4-benzoquinone as a bright yellow crystalline solid m.p. 85°–7° C. with the following percentage composition by weight.

|  | Carbon | Hydrogen |
|---|---|---|
| Found | 67.56 | 8.20 |
| Calculated for $C_{22}H_{32}O_6$ | 67.32 | 8.22 |

EXAMPLE 2c 3.9 Parts of 2,5-bis-(5'-methoxycarbonyl-2'-methyl-pent-2'-yl)-hydroquinone (Example 2a), 0.4 parts of 2,5-bis-(5'-methoxycarbonyl-2'-methyl-pent-2'-yl)-1,4-benzoquinone (Example 2b), 1.0 parts of p-toluene sulphonic acid, and 50 parts of methanol are refluxed for 48 hours. After removing the excess methanol under reduced pressure, the residue is taken up in ether, and the ether extract washed first with sodium carbonate solution and then water. Evaporation of the ether gives a solid residue which is shown by GLC analysis to have the following percentage composition by weight.

| Compound | % |
|---|---|
| 2,5-bis-(5'-methoxycarbonyl-2'-methyl-pent-2'-yl)-1,4-dimethoxybenzene | 21.3 |
| 2,5-bis-(5'-methoxycarbonyl-2'-methyl-pent-2'-yl)-4-methoxyphenol | 67.0 |
| 2,5-bis-(5'-methoxycarbonyl-2'-methyl-pent-2'-yl)-hydroquinone | 11.7 |

Crystallisation of the above solid mixture from 40°-60° petroleum-ether gives the 2,5-bis-(5'-methoxycarbonyl-2'-methyl-pent-2'-yl)-4-methoxyphenol m.p. 81°-3° C. identical with that obtained in Example 1.

EXAMPLE 3

3.5 Parts of 2,5-bis-(5'-methoxycarbonyl-2'-methyl-pent-2'-yl)-4-methoxyphenol, 100 parts of n-hexanol, and 0.5 parts of p-toluene sulphonic acid are heated on a steam-bath for 48 hours. At the end of the heating period the excess hexanol is removed by rota-evaporator under reduced pressure, and the residual oil taken up in ether. The ether solution is washed first with sodium bicarbonate solution then with water, and evaporated. Short-path distillation of the residue gives 2,5-bis-(5'-n-hexyloxycarbonyl-2'-methyl-pent-2'-yl)-4-methoxyphenol as a pale yellow viscous oil with the following percentage composition by weight.

| | Carbon | Hydrogen |
|---|---|---|
| Found | 72.33 | 10.45 |
| Calculated for $C_{33}H_{56}O_6$ | 72.22 | 10.29 |

EXAMPLE 4

2.3 Parts of 2,5-bis-(5'-carboxy-2'-methyl-pent-2'-yl)-4-methoxyphenol, 50 parts of tetrahydrofurfuryl alcohol and 0.2 parts of p-toluene sulphonic acid are heated on a steam-bath for 18 hours. The excess alcohol is then removed by rota-evaporator under reduced pressure, and the residual oil taken up in ether. The ether solution after being washed with sodium bicarbonate solution and water is then evaporated to leave 2,5-bis-(5'-tetrahydrofurfuryloxycarbonyl-2'-methyl-pent-2'-yl)-4-methoxyphenol as an oil with the following percentage composition by weight.

| | Carbon | Hydrogen |
|---|---|---|
| Found | 67.97 | 9.09 |
| Calculated for $C_{31}H_{48}O_8$ | 67.86 | 8.82 |

EXAMPLE 5

2,5-Bis-(5'-n-butoxyethoxycarbonyl-2'-methyl-pent-2'-yl)-4-methoxyphenol is prepared by the procedure described in Example 4 using n-butoxyethanol in place of the tetrahydrofurfuryl alcohol. This ester obtained as an oil has the following percentage composition by weight.

| | Carbon | Hydrogen |
|---|---|---|
| Found | 68.33 | 9.67 |
| Calculated for $C_{33}H_{56}O_8$ | 68.24 | 9.72 |

EXAMPLE 6

(a) Example 1 is repeated using 13.8 parts of hydroquinone mono-ethyl ether in place of the hydroquinone mono-methyl ether. In this way there is obtained, 2,5-bis-(5'-methoxycarbonyl-2'-methyl-pent-2'-yl)-4-ethoxyphenol as an oil, $b_{0.7}$ 210° C. (short-path distillation). ($b_{0.7}$=boiling point at 0,7 millibar).

| | Carbon | Hydrogen |
|---|---|---|
| Found | 68.45 | 9.31 |
| Calculated for $C_{24}H_{38}O_6$ | 68.22 | 9.06 |

(b) In a similar manner to Example 1b there is obtained 2,5-bis-(5'-carboxy-2'-methyl-pent-2'-yl)-4-ethoxyphenol with m.p. 169°-71° C.

| | Carbon | Hydrogen |
|---|---|---|
| Found | 67.13 | 8.72 |
| Calculated for $C_{22}H_{34}O_6$ | 66.98 | 8.69 |

EXAMPLE 7

The acid of Example 6b is esterified with ethanol by the procedure of Example 4 to give 2,5-bis-(5'-ethoxycarbonyl-2'-methyl-pent-2'-yl)-4-ethoxyphenol and has m.p. 52°-4° C. from 40°-60° petroleum-ether.

| | Carbon | Hydrogen |
|---|---|---|
| Found | 69.91 | 9.44 |
| Calculated for $C_{26}H_{42}O_6$ | 69.30 | 9.36 |

EXAMPLE 8

In a similar manner to Example 4 the acid of Example 6b is reacted with n-hexanol to give 2,5-bis-(5'-n-hexyloxycarbonyl-2'-methyl-pent-2'-yl)-4-ethoxyphenol as an oil after a short-path distillation at 0.7 mb.

| | Carbon | Hydrogen |
|---|---|---|
| Found | 72.61 | 10.39 |
| Calculated for $C_{34}H_{58}O_6$ | 72.56 | 10.39 |

EXAMPLE 9

In a similar manner to Example 1a and 1b using 16.6 parts of hydroquinone mono-n-butyl ether in place of hydroquinone monomethyl ether there is obtained:

(a) 2,5-Bis-(5'-methoxycarbonyl-2'-methyl-pent-2'-yl)-4-n-butoxyphenol $b_{0.9}$ 238°-40° C.

| | Carbon | Hydrogen |
|---|---|---|
| Found | 69.33 | 9.52 |
| Calculated for $C_{26}H_{42}O_6$ | 69.30 | 9.39 | and (b) 2,5-bis-(5'-carboxy-2'-methyl-pent-2'-yl)-4-n-butoxyphenol m.p. 141°-3° C. from glacial acetic acid/water.

|  | Carbon | Hydrogen |
| --- | --- | --- |
| Found | 68.12 | 9.19 |
| Calculated for $C_{24}H_{38}O_6$ | 68.22 | 9.06 |

(c) The acid from 9b is esterified with isopropanol by the procedure of Example 4 to give 2,5-bis-(5'-isopropyloxycarbonyl-2'-methyl-pent-2'-yl)-4-n-butoxyphenol with m.p. 62°-4° from 40°-60° petroleum-ether at −20° C.

|  | Carbon | Hydrogen |
| --- | --- | --- |
| Found | 71.37 | 10.00 |
| Calculated for $C_{30}H_{50}O_6$ | 71.11 | 9.95 | and (d) The acid from 9b is esterified with n-hexanol in the manner described in Example 4 to give 2,5-bis-(5'-n-hexyloxycarbonyl-2'-methyl-pent-2'-yl)-4-n-butoxyphenol as an oil after a short-path distillation at 0.3 mb

|  | Carbon | Hydrogen |
| --- | --- | --- |
| Found | 73.09 | 10.51 |
| Calculated for $C_{36}H_{62}O_6$ | 73.18 | 10.58 |

EXAMPLE 10

62.0 Parts of hydroquinone monomethyl ether, 28.4 parts of methyl 5-methyl-hex-4-enoate, and 2.0 parts of p-toluene sulphonic acid are heated on a steam-bath for 5 days. The reaction mixture is then diluted with ether and washed first with 2N sodium hydroxide solution and then water. After evaporation of the ether, the residue is distilled to give 2-(5'-methoxycarbonyl-2'-methyl-pent-2'-yl)-4-methoxyphenol with $b_{0.1}$ 154° C. and the following percentage composition by weight.

|  | Carbon | Hydrogen |
| --- | --- | --- |
| Found | 67.92 | 8.56 |
| Calculated for $C_{15}H_{22}O_4$ | 67.65 | 8.33 |

Acidification of the above alkaline washings gives an oil which after isolation with ether is distilled to give 3-(5'-methoxycarbonyl-2'-methyl-pent-2'-yl)-4-methoxyphenol $b_{0.4}$ 172° C.

|  | Carbon | Hydrogen |
| --- | --- | --- |
| Found | 67.47 | 8.32 |
| Calculated for $C_{15}H_{22}O_4$ | 67.65 | 8.33 |

EXAMPLE 11

To 6.8 parts of aluminium chloride dissolved in 25 parts of nitromethane is added 13.8 parts of hydroquinone dimethyl ether and 7.1 parts of methyl 5-methyl-hex-5-enoate dissolved in 25 parts nitromethane dropwise at room temperature. The reaction mixture is then stored at room temperature for 2 days before being poured into water. The organic phase is ether extracted, and the ether extract is washed in turn with water, 2N sodium hydroxide solution, water, and then evaporated. Distillation of the residue gives 2-(5'-methoxycarbonyl-2'-methyl-pent-2'-yl)-1,4-dimethoxybenzene with $b_{0.4}$ 150° C. and the following percentage composition by weight.

|  | Carbon | Hydrogen |
| --- | --- | --- |
| Found | 68.66 | 8.66 |
| Calculated for $C_{16}H_{24}O_4$ | 68.55 | 8.63 |

EXAMPLE 12

The procedure described in Example 10 is repeated using twice the quantities of aluminium chloride and methyl 5-methyl-hex-5-enoate and gives bis-2,5-(5'-methoxycarbonyl-2'-methyl-pent-2'-yl)-1,4-dimethoxybenzene m.p. 81°-3° C. after crystallisation from 40°-60° petroleum ether

|  | Carbon | Hydrogen |
| --- | --- | --- |
| Found | 68.48 | 9.12 |
| Calculated for $C_{24}H_{38}O_6$ | 68.22 | 9.06 |

EXAMPLE 13

2.5 Parts of 2-(5'-methoxycarbonyl-2'-methyl-pent-2'-yl)-hydroquinone, 1.5 parts of 2,5-dimethylhexa-2,4-diene, and 0.1 parts of p-toluene sulphonic acid are heated on a steam-bath for 3 days. The reaction after dilution with ether is washed first with 2N sodium hydroxide, followed by water, and the ether evaporated. Short path distillation of the residue at 0.3 mb gives 1.7 parts of lower boilers with the oven temperature at 175°, and then 6-hydroxy-7-(5'-methoxycarbonyl-2'-methyl-pent-2'-yl)-2,2-dimethyl-4-isopropylchroman with the oven temperature at 250°.

|  | Carbon | Hydrogen |
| --- | --- | --- |
| Found | 72.15 | 9.56 |
| Calculated for $C_{22}H_{34}O_4$ | 72.89 | 9.45 |

EXAMPLE 14

24.8 parts of p-methoxyphenol, 15.1 parts of citronellyl nitrile and 2.0 parts of p-toluene sulphonic acid are heated on a steam-bath for 3 days. The reaction mixture is then diluted with ether and the ether solution washed with sodium bicarbonate solution and water. After evaporation of the ether, the residue is distilled to give a mixture of 2- and 3-(7'-cyano-2',6'-dimethyl-hept-2'-yl)-4-methoxyphenol $b_{0.3}$ 178°-86° C.

|  | Carbon | Hydrogen | Nitrogen |
| --- | --- | --- | --- |
| Found | 74.14 | 9.15 | 5.09 |
| Calculated for $C_{17}H_{25}NO_2$ | 73.91 | 9.39 | 5.18 |

EXAMPLE 15

To a stirred suspension of 4.0 parts of lithium aluminium hydride in 100 parts of ether, there is added 5.5 parts of 2- and 3-(7'-cyano-2',6'-dimethyl-hept-2'-yl)-4-methoxyphenol from Example 14, in 50 parts of ether, dropwise over 30 minutes. On completing the addition, stirring is continued for a further 2 hours before ethyl acetate is added to destroy unreacted lithium aluminium hydride. To the reaction mixture is then added 100 parts of 10N sodium hydroxide solution and the aqueous phase separated off from the ether solution. After washing the ether solution with water, the ether is evaporated and the residue distilled to give a mixture of 2- and 3-(8'-amino-2',6'-dimethyl-oct-2'-yl)-4-methoxyphenol $b_{0.7}$ 182°–5° C. as a colourless oil with the following percentage composition by weight.

|  | Carbon | Hydrogen | Nitrogen |
|---|---|---|---|
| Found | 72.91 | 10.46 | 4.80 |
| Calculated for $C_{17}H_{29}NO_2$ | 73.07 | 10.46 | 5.01 |

EXAMPLE 16

By the same procedure of Example 15, 9.2 parts of 2,5-bis-(5'-methoxycarbonyl-2'-methyl-pent-2'-yl)-4-ethoxyphenol is reduced with 4.0 parts of lithium aluminium hydride and gives 2,5-bis-(6'-hydroxy-2'-methyl-hex-2'-yl)-4-ethoxyphenol $b_{0.7}$ 230° C. as a pale yellow oil with the following percentage composition by weight.

|  | Carbon | Hydrogen |
|---|---|---|
| Found | 72.16 | 10.69 |
| Calculated for $C_{22}H_{38}O_4$ | 72.09 | 10.45 |

EXAMPLE 17

62 parts of p-methoxyphenol, 17.8 parts of dimethylprenyl phosphonate, and 5.0 parts of Fulcat 22 ® are stirred at 125°–30° C. for 24 hours. The reaction mixture, after cooling, is diluted with methanol and filtered free of the catalyst. After removing the methanol under reduced pressure on a rota-evaporator, the residual oil is distilled to remove unreacted p-methoxyphenol ($b_{0.7}$ 115° C.). The residual oil is then chromatographed on a column prepared from 200 parts of silica made up in 40°–60° petroleum ether. Elution with petroleum and then with petroleum containing increasing amounts of ether gives 2-(2'-methyl-4'-dimethylphosphono-but-2'-yl)-4-methoxyphenol as white prisms m.p. 97°–9° C. from ether.

|  | Carbon | Hydrogen | Phosphorous |
|---|---|---|---|
| Found | 56.00 | 7.52 | 10.13 |
| Calculated for $C_{14}H_{23}O_5P$ | 55.62 | 7.67 | 10.25 |

EXAMPLE 18

12.4 parts of p-methoxyphenol and 9.4 parts of N-acetylheptaminol are reacted together using the procedure of Example 1 and gives, as product, a mixture of 2- and 3-(6'-acetamido-2'-methylhept-2'-yl)-4-methoxyphenol. The 2-isomer is obtained as a white crystalline solid m.p. 118°–20° C. after crystallisation from ether containing a little acetone.

|  | Carbon | Hydrogen | Nitrogen |
|---|---|---|---|
| Found | 69.65 | 9.62 | 4.87 |
| Calculated for $C_{17}H_{27}NO_3$ | 69.59 | 9.28 | 4.77 |

EXAMPLE 19

8.2 parts of 2,5-bis-(5'-methoxycarbonyl-2'-methyl-pent-2'-yl)-4-methoxyphenol and 50 parts of n-octylamine are refluxed together for 20 hours. After removing the excess octylamine under reduced pressure, the residue is diluted with 40°–60° petroleum-ether containing a little ether and gives 2,5-bis-(5'-N-n-octylcarbamoyl-2'-methyl-pent-2'-yl)-4-methoxyphenol m.p. 86°–90° C.

|  | Carbon | Hydrogen | Nitrogen |
|---|---|---|---|
| Found | 73.54 | 11.88 | 4.81 |
| Calculated for $C_{37}H_{66}N_2O_4$ | 73.71 | 11.03 | 4.65 |

EXAMPLE 20

5.0 parts of 2,5-bis-(5'-methoxycarbonyl-2'-methyl-pent-2'-yl)-4-methoxyphenol and 20 parts of di-n-butylamine are sealed into a glass tube and heated at 200° C. for 48 hours. The excess dibutylamine is removed under reduced pressure and gives 2,5-bis-(5'-N,N-di-n-butylcarbamoyl-2'-methyl-pent-2'-yl)-4-methoxyphenol as a pale yellow viscous syrup with the following percentage composition by weight:

|  | Carbon | Hydrogen | Nitrogen |
|---|---|---|---|
| Found | 73.80 | 10.91 | 4.38 |
| Calculated for $C_{37}H_{66}N_2O_4$ | 73.71 | 11.03 | 4.65 |

EXAMPLE 21

24.8 parts of p-methoxyphenol, 13.8 parts of 4-acetyl-1-methylcyclohex-1-ene and 2.0 parts of p-toluene sulphonic acid are heated on a steam-bath for 3 days and the reaction mixture then diluted with ether. After washing the ether extract with 2N sodium hydroxide, and water, the ether is evaporated and the residue distilled to give a mixture of cis- and trans-2-(4'-acetyl-1'-methylcyclohex-1'-yl)-4-methoxyphenol $b_{0.3}$ 200°–20° C.

|  | Carbon | Hydrogen |
|---|---|---|
| Found | 75.81 | 8.96 |
| Calculated for $C_{16}H_{22}O_3$ | 73.25 | 8.45 |

EXAMPLE 22

Example 21 is repeated except that 21.2 parts of 4,5-bis-carbomethoxy-1-methylcyclohex-1-ene is used in place of the 4-acetyl-1-methyl-cyclohex-1-ene. Distillation gives 2- and 3-(3',4'-bis-methoxycarbonyl-1'-methyl-cyclohex-1'-yl)-4-methoxyphenol $b_{0.3}$ 218°–24° C.

|  | Carbon | Hydrogen |
|---|---|---|
| Found | 64.23 | 7.44 |
| Calculated for $C_{18}H_{24}O_6$ | 64.27 | 7.19 |

EXAMPLE 23

10.0 parts of 2,5-bis-(5'-methoxycarbonyl-2'-methyl-pent-2'-yl)-4-methoxyphenol, 50 parts of cetyl alcohol and 1.0 parts of p-toluene sulphonic acid are heated on a steam-bath for 3 days. At the end of the heating period most of the excess cetyl alcohol is removed by rota-evaporator under reduced pressure, and the residual oil taken up in ether. The ether solution is washed first with sodium bicarbonate solution then with water and evaporated. The residual oil is finally stripped down on a rotary-still at 0.7 mb at a temperature of 230° C., and gives 2,5-bis-(5'-hexadecycloxycarbonyl-2'-methyl-pent-2'-yl)-4-methoxyphenol as a viscous oil with the following percentage composition by weight.

|  | Carbon | Hydrogen |
| --- | --- | --- |
| Found | 77.15 | 11.90 |
| Calculated for $C_{53}H_{96}O_6$ | 76.81 | 11.59 |

EXAMPLE 24

Example 17 is repeated except that 30.6 parts of diethyl 2-ethoxycarbonyl-5-methyl-hex-4-ene-2-phosphonate are used in place of dimethyl prenyl phosphonate, and there is obtained 2- and 3-(5'-ethoxycarbonyl-5'-diethylphosphono-2'-methyl-pent-2'-yl)-4-methoxyphenol as a viscous oil.

|  | Carbon | Hydrogen | Phosphorous |
| --- | --- | --- | --- |
| Found | 58.51 | 8.12 | 6.95 |
| Calculated for $C_{21}H_{35}O_7P$ | 58.59 | 8.19 | 7.19 |

EXAMPLE 25

5.0 parts of 2-(5'-methoxycarbonyl-2'-methyl-pent-2'-yl)-hydroquinone, 1.9 parts 1,4-bis-(2'-hydroxy-prop-2'-yl)-benzene, and 0.2 parts of p-toluene sulphonic acid in 25 parts of benzene are refluxed for 24 hours. The reaction mixture after cooling is diluted with ether, and the ether solution washed with 2N sodium hydroxide solution, and water. Evaporation of the ether gives a solid residue which, after crystallisation from benzene, gives 1,4-bis-{2-[2,5-dihydroxy-4-(5'-methoxycarbonyl-2'-methyl-pent-2'-yl)-phenyl]-prop-2-yl}-benzene m.p. 198°–201° C.

|  | Carbon | Hydrogen |
| --- | --- | --- |
| Found | 72.68 | 8.39 |
| Calculated for $C_{40}H_{54}O_8$ | 72.48 | 8.21 |

EXAMPLE 26

6.9 parts of hydroquinone dimethyl ether, 6.2 parts of N-n-octyl-2-propene-1-sulphonic acid amide and 13.4 parts of anhydrous aluminium chloride in 50 parts of nitromethane are stored for 3 days at room temperature. The reaction mixture is then poured into water and the organic material extracted with ether. After washing the ether extract with water and evaporating off solvents, the residue is chromatographed on silica and gives 2-(2'-methyl-3'-N-n-octylsulphonamido-prop-2'-yl)-4-methoxyphenol as a viscous oil.

|  | Carbon | Hydrogen | Nitrogen |
| --- | --- | --- | --- |
| Found | 62.17 | 8.83 | 3.83 |
| Calculated for $C_{20}H_{35}NO_4S$ | 62.30 | 9.15 | 3.63 |

EXAMPLE 27

13.3 parts of 2-(5'-methoxycarbonyl-2'-methyl-pent-2'-yl)-4-methoxyphenol and 2.9 parts of hexamethylenediamine are heated at 150° C. for 24 hours. The cooled reaction product is then triturated with 40°–60° petroleum-ether and yields N-N'-[5-(2'-hydroxy-5'-methoxyphenyl)-5-methyl-hexanoic acid amide] of hexane-1,6-diamine m.p. 58°–60° C.

|  | Carbon | Hydrogen | Nitrogen |
| --- | --- | --- | --- |
| Found | 69.72 | 9.62 | 4.48 |
| Calculated for $C_{34}H_{52}N_2O_6$ | 69.83 | 8.96 | 4.79 |

EXAMPLE 28

2.4 parts of 2,5-bis-(6'-hydroxy-2'-methyl-hex-2'-yl)-4-ethoxyphenol, (from example 16), in 15 parts benzene, are treated with 10 parts of acetyl chloride in 5 parts benzene. After storing overnight at room temperature, the benzene is removed and the residue, after short-path distillation at 0.7 mb, gives 2,5-bis-(6'-acetoxy-2'-methyl-hex-2'-yl)-4-ethoxyphenol as a pale yellow viscous oil.

|  | Carbon | Hydrogen |
| --- | --- | --- |
| Found | 69.38 | 9.39 |
| Calculated for $C_{26}H_{42}O_6$ | 69.30 | 9.39 |

EXAMPLE 29

(a) 4.3 parts of 3-(5'-methoxycarbonyl-2'-methyl-pent-2'-yl)-4-methoxy phenol (from example 10), 2.0 parts of isobutylene and 0.2 part of p-toluene sulphonic acid in 25 parts of benzene are sealed into a glass tube and heated at 100° C. for 40 hours. The cooled reaction mixture is diluted with ether, and the ether solution is washed with 2N sodium hydroxide and water. Evaporation of the ether and benzene gives 2-t-butyl-5-(5'-methoxycarbonyl-2'-methyl-pent-2'-yl)-4-methoxyphenol as a white crystalline solid, m.p. 71°–3° C. from 60°–80° C. petroleum ether.

|  | Carbon | Hydrogen |
| --- | --- | --- |
| Found | 70.65 | 9.62 |
| Calculated for $C_{19}H_{30}O_4$ | 70.77 | 9.38 |

(b) 2-t-butyl-5-(5'-methoxycarbonyl-2'-methyl-pent-2'-yl)-4-methoxy phenol from example 29a) is transesterified with n-hexanol by the procedure of example 3. Short-path distillation at 1 mb gives 2-t-butyl-5-(5'-n-hexyloxycarbonyl-2'-methyl-pent-2'-yl)-4-methoxyphenol as a pale yellow viscous oil with the following percentage composition by weight:

|  | Carbon | Hydrogen |
| --- | --- | --- |
| Found | 73.76 | 10.51 |
| Calculated for $C_{24}H_{40}O_4$ | 73.43 | 10.27 |

EXAMPLE 30

(a) 2-cumyl-5-(5'-methoxycarbonyl-2'-methyl-pent-2'-yl)-4-methoxy phenol m.p. 102°–4° C. from petroleum ether, is obtained from alphamethyl styrene and 3-(5'-methoxycarbonyl-2'-methyl-pent-2'-yl)-4-methoxyphenol by the procedure of example 29.

|  | Carbon | Hydrogen |
|---|---|---|
| Found | 75.21 | 8.49 |
| Calculated for C$_{24}$H$_{32}$O$_4$ | 74.97 | 8.39 |

(b) 2-cumyl-5-(5'-n-hexyloxycarbonyl-2'-methyl-pent-2'-yl)-4-methoxyphenol is obtained by transesterification of the methyl ester from example 30a) with n-hexanol using the procedure of example 3, and is obtained as a pale yellow viscous oil after short-path distillation at 0.7 mb.

|  | Carbon | Hydrogen |
|---|---|---|
| Found | 76.62 | 9.21 |
| Calculated for C$_{29}$H$_{42}$O$_4$ | 76.61 | 9.31 |

EXAMPLE 31

2.5 parts of 2-(5'-methoxycarbonyl-2'-methyl-pent-2'-yl)-hydroquinone, 0.68 part isoprene, 0.1 part p-toluene sulphonic acid and 15 parts benzene are sealed into a glass tube and heated at 80° C. for 3 days. The product is worked up as in example 13 and gives 6-hydroxy-7-(5'-methoxycarbonyl-2'-methyl-pent-2'-yl)-2,2-dimethylchroman as a pale yellow oil after short-path distillation at 0.7 mb

|  | Carbon | Hydrogen |
|---|---|---|
| Found | 71.44 | 8.84 |
| Calculated for C$_{19}$H$_{28}$O$_4$ | 71.22 | 8.81 |

Use Example 1: 0.05 mMol of the magenta coupler of the following formula

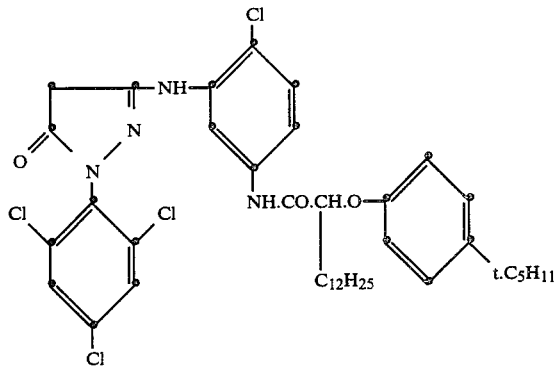

and 0.025 mMol of the compound of formula I are dissolved in 2.0 ml of tricresylphosphate/ethyl acetate (0.75 g/100 ml). 7.0 ml of a 6% gelatin solution, 1.0 ml of a 0.8% solution of the wetting agent of the formula

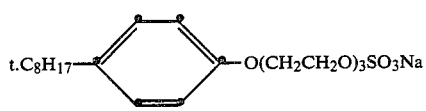

are put into water, then emulsified for 5 minutes by means of a 100-Watt ultra-sonic appliance. 2.5 ml of coupler-additive emulsion, freshly treated in the ultra-sonic appliance, 2.0 ml of silver bromide emulsion with a content of 0.6% silver, 0.7 ml of a 1% aqueous solution of the curing agent with the following formula

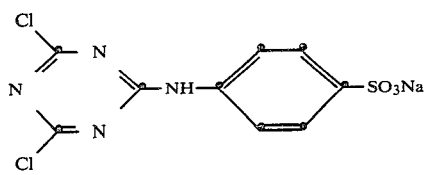

and 2.8 ml of water are mixed together, set to a pH value of 6.5, and at 40° C. poured onto a polyethylene paper measuring 14–18 cm. After the coating has hardened at 10° C., the poured-on mixture is dried at room-temperature.

PROCESSING

The samples of the coated paper obtained are exposed to light of 500 Lux under a step-wedge for 6 seconds and then processed as follows at 32.8° C. (−0.3° C.):

| 1. Developer bath | 3.5 minutes |
|---|---|
| 2. Bleaching fixing bath | 1.5 minutes |
| 3. Washing | 3.0 minutes |
| 4. Drying | 1.0 minutes |

The developer bath has the following composition: 4-amino-3-methyl-N-ethyl-N-[β-(methyl-sulphonamido)ethyl]-aniline

| 1½ H$_2$SO$_4$.H$_2$O | 4.85 (g/liter) |
|---|---|
| Potassium bromide | 0.6 |
| Potassium carbonate | 32.0 |
| Lithium sulphate | 1.8 |
| Potassium sulphite | 2.0 |
| Hydroxylaminesulphite | 3.9 |
| Ethyleneglycol | 21.3 |
| Benzyl alcohol | 15.1 |
| Water | to 1 liter |
| The pH value is 10.1 | |

The bleaching fixing bath used is a conventional bath, with e.g. the following composition:

| Ammoniumthiosulphate (80% solution) | 200 (g/liter) |
|---|---|
| Sodium sulphite (anhydrous) | 15 |
| Sodium carbonate (anhydrous) | 2.5 |
| Ethylenediamine tetra-acetic acid, sodium salt | 2 |
| Ethylenediamine tetra-acetic acid sodium-iron-(III)-salt | 50 |
| Water | to 1 liter |

After washing and drying, clear, sharp magenta wedges are obtained with absorption maximum at 537 nm and maximum reflectance densities of 1.80.

A step-wedge obtained in this way is illuminated in an Atlas weather ometer (2500 W lamp) with a total energy of 42 kJ/cm$^2$ through an ultra-violet filter (Kodak Wratten 2C). For comparison, a step-wedge prepared analogously, which contains no compound according to the invention, is used.

In all cases the residual optical density (OD) was measured in % of the initial density (initial density 1.0). Table 1 contains the results.

TABLE 1

Light Stabilising Effect of Compounds of Formula I

| compound of formula I, product of | % OD (with UV filter; 42 kJ/cm$^2$) |
|---|---|
| none | 47 |
| Example 1a | 86 |
| Example 3 | 90 |
| Example 4 | 90 |
| Example 5 | 85 |
| Example 6a | 85 |
| Example 7 | 86 |
| Example 8 | 90 |
| Example 9a | 88 |
| Example 9c | 89 |
| Example 13 | 91 |

Compared with the emulsion without stabiliser, emulsions containing the compounds of formula I are more stable to light.

Use Example 2: A coating is prepared according to Use Example 1, which contains 0.0125 mMol of the compound of Example 3 and 0.0125 mMol of the compound of formula A

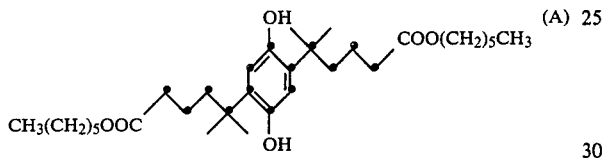

instead of 0.025 mMol of one of the products of the Examples 1 to 5, and exposed, processed and illuminated as described in Use Example 1. The remaining density is 89 percent of an original density of 1.0.

The compound of formula A is prepared as follows:

5.5 Parts of hydroquinone, 21.2 parts of n-hexyl 5-methyl-hex-5-enoate, and 1.0 parts of p-toluene sulphonic acid are heated on a steam-bath for 4 days. The cooled reaction mixture is taken up in ether, washed with 10% sodium hydroxide solution and then with water, until neutral. After stripping, the residual oil which partially solidifies, is triturated with 40°-60° petroleum ether and gives 2,5-bis-(5'-n-hexyloxycarbonyl-2'-methyl-pent-2'-yl)-hydroquinone m.p. 77°-8° C. A further crystallisation from 60°-80° petroleum ether gives material m.p. 83°-6° C.

|  | Carbon | Hydrogen |
|---|---|---|
| Found | 71.77 | 10.23 |
| Calculated for $C_{32}H_{54}O_6$ | 71.87 | 10.18 |

Use Example 3: Coatings are produced according to Use Example 1 with a molar coupler to stabilizer ratio of 2:1 and exposed through a Kodak Photographic Step Tablet No. 2. Table 2 contains the green reflectance densities of the steps No. 3, 5 and 7.

TABLE 2

Dye yield in the presence of substituted hydroquinone ethers

| Product | Reflectance density | | |
|---|---|---|---|
|  | step 3 | step 5 | step 7 |
| none | 52 | 90 | 134 |
| Example 1a | 51 | 94 | 138 |
| Example 7 | 53 | 91 | 142 |
| Example 8 | 51 | 88 | 132 |

It can be clearly seen that the products of the invention have no influence on dye yield.

Use Example 4: In an analogous series of experiments to those described in Use. Example 1 a further compound of formula I is evaluated and the result given in Table 3.

TABLE 3

Light stabilising effect of the compound of Example 12

| Compound of Formula I Hydroquinone Ether | % OD (with UV filter; 42 kJ/cm$^2$) |
|---|---|
| Without light stabiliser | 45 |
| Product of Example 12 | 83 |

What is claimed is:

1. A compound having the formula I

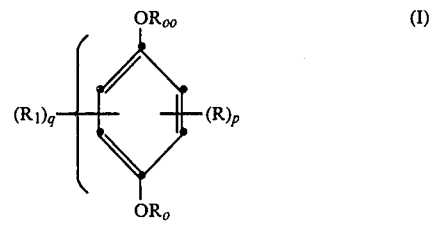

wherein p is 1 or 2 and q is 0 or 1, provided that p+q is 1 or 2; R is a residue of formula II

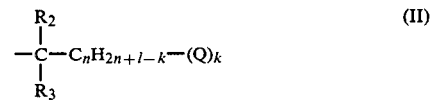

wherein Q is selected from the residues:

(i) —OX wherein X is $R_7$ or —$COR_7$, wherein $R_7$ is —H or a $C_1$–$C_{20}$ straight or branched chain alkyl group, a $C_3$–$C_{20}$ straight or branched chain alkenyl group, a $C_3$–$C_{12}$ cycloalkyl group, a $C_7$–$C_{13}$ aralkyl group, or a $C_6$–$C_{10}$ aryl group, optionally substituted by one or two $C_1$–$C_4$ alkyl groups;

(ii) —N($R_8$)($R_9$) wherein $R_8$ and $R_9$ independently, are —H or a $C_1$–$C_{20}$ straight or branched chain alkyl group, a $C_3$–$C_{20}$ straight or branched chain alkenyl group, a $C_3$–$C_{12}$ cycloalkyl group, a $C_7$–$C_{13}$ aralkyl group or a $C_6$–$C_{10}$ aryl group optionally substituted by one or two $C_1$–$C_4$ alkyl groups, or an acyl group of formula —$COR_7$ wherein $R_7$ has its previous significance, or $R_8$ and $R_9$, together with the nitrogen atom to which they are each bonded, form a 5- or 6-membered heterocyclic ring, optionally substituted by one or two $C_1$–$C_4$ alkyl groups;

(iii) —$SO_2R_{12}$ wherein $R_{12}$ is —OH, —Cl or —N($R_5$)($R_7$) wherein $R_5$ is hydrogen, a straight or branched chain $C_1$–$C_{20}$ alkyl group or a $C_5$–$C_6$ cycloalkyl group and $R_7$ is as previously defined; provided that, when $R_{12}$ is —OH, then $R_1$ is a residue of formula II; and (iv) —$NO_2$; n is an integer from 1 to 20; k is 1 or 2; $R_2$ and $R_3$ are the same or different and each is straight or branched chain alkyl group having from 1 to 5 carbon atoms; $R_1$ is $C_1$–$C_8$ straight or branched chain alkyl, $C_5$–$C_7$ cycloalkyl optionally substituted by one or two methyl or ethyl groups, $C_7$–$C_9$ aralkyl or a residue of formula II as hereinbefore defined, and when $R_1$ is a residue of formula II then $R_1$ and R may be the same or different; or $R_1$ is a residue of formula III:

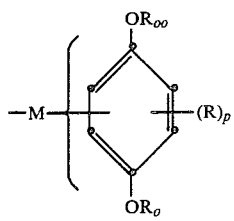

in which R and p have their previous significance; and M is a direct bond; $-C(R_{13})(R_{14})-$ in which $R_{13}$ and $R_{14}$ are the same or different and are hydrogen, $C_1$-$C_{20}$ straight or branched chain alkyl optionally interrupted by 1 to 3 sulphur atoms, $C_6$-$C_{10}$ aryl or $R_{13}$ and $R_{14}$, together with the carbon atom to which they are attached may form a 5- or 6-membered ring which may be further substituted by one or two $C_1$-$C_8$ straight or branched chain alkyl groups; $-S-$; $-S-S-$; $-SO_2-$; $-CH_2SCH_2-$; $-CH_2OCH_2-$ or $-C(CH_3)_2$-p-phenylen-$C(CH_3)_2-$; $R_o$ and $R_{oo}$ are the same or different and each is hydrogen, a $C_1$-$C_{20}$ straight or branched chain alkyl group optionally interrupted by 1 to 5 oxygen atoms, a $C_3$-$C_{12}$ cycloalkyl group, a $C_6$-$C_{10}$aryl group optionally substituted by one or two $C_1$-$C_4$ straight or branched chain alkyl groups, or a $C_7$-$C_{13}$aralkyl group provided that both of $R_o$ and $R_{oo}$ are not hydrogen, or $R_{oo}$ has its previous significance and $R_o$ is a residue of formula IV:

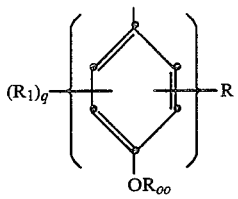

in which R, $R_{oo}$, $R_1$ and q have their previous significance, or $R_o$ and $R_1$, when in ortho position to one another, together with the carbon atoms to which they are attached, may form an optionally substituted residue of formula V:

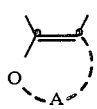

wherein A is a carbon residue containing 4 to 20 carbon atoms which forms a substituted chroman or coumaran system, or $R_o$ and $R_1$ together may form a residue having the formula VI or VII:

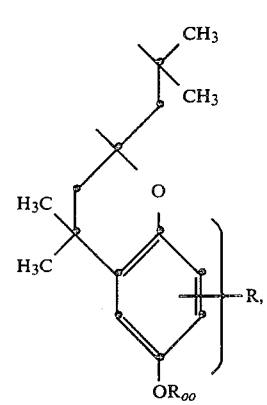

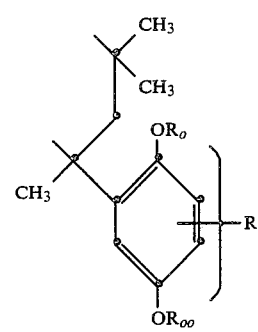

wherein R, $R_o$ and $R_{oo}$ have their previous significance, provided that the compound of formula I contains only one residue of formula III or IV; or $R_{oo}$ is hydrogen and $R_o$ is a residue having the formula IVa or IVb:

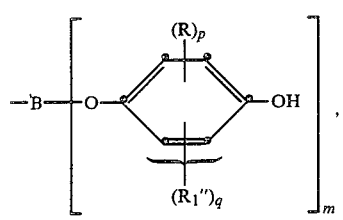

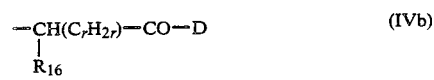

wherein p, q and R have their previous significance, $R_1''$ is $C_1$-$C_8$ straight or branched alkyl, $C_7$-$C_9$ aralkyl or a residue of formula II, as hereinbefore defined, m is 1 or 2, B, when m is 1, represents $C_2$-$C_{12}$ alkylene which may be interrupted by 1 to 3 oxygen or sulphur atoms, $C_4$-$C_{10}$ alkenylene, $C_5$-$C_{12}$ cycloalkylene, $C_6$-$C_{12}$arylene, $C_8$-$C_{12}$ aralkylene, $C_{4\text{-}6}$alkynylene, xylylene, $-CH_2CH(OH)CH_2-$, $-CH_2CH(OH)CH_2-O-Y-O-CH_2CH(OH)CH_2-$,

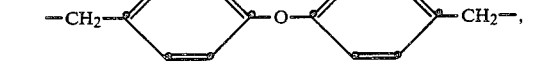

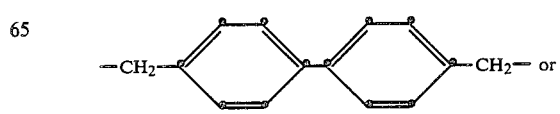

-continued

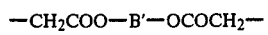

wherein Y is $C_2$-$C_{10}$alkylene, $C_6$-$C_{12}$ arylene,

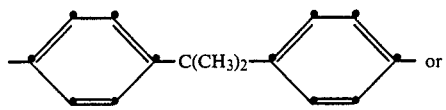

$C_6$-$C_{12}$ cycloalkylene,

B' is $C_2$-$C_8$alkylene, $C_4$-$C_8$ oxaalkylene, or cyclohexylene and, when m is 2, B represents a group of the formula

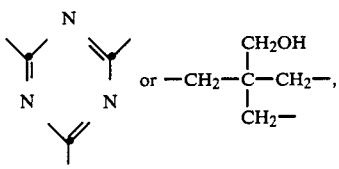

r is 0 to 12, $R_{16}$ represents hydrogen or straight or branched $C_1$-$C_{12}$alkyl and D is —$OR_4$ or —$N(R_4)(R_5)$ wherein $R_4$ independently is (1) —H, (2) a $C_1$-$C_{20}$ straight or branched chain alkyl optionally interrupted by 1 to 5 oxygen atoms and optionally substituted by a group —$OR_6$ wherein $R_6$ is $C_3$-$C_{12}$ cycloalkyl, straight or branched $C_3$-$C_{20}$ alkenyl, $C_6$-$C_{10}$ aryl optionally substituted by one or two $C_1$-$C_4$ alkyl groups or $C_7$-$C_{13}$ aralkyl, (3) a $C_2$-$C_{20}$ divalent straight or branched chain alkylene residue, (4) a $C_3$-$C_{20}$ straight or branched chain alkenyl group, (5) a $C_3$-$C_{12}$ cycloalkyl group, (6) a $C_6$-$C_{10}$ aryl group optionally substituted by one or two $C_1$-$C_8$ alkyl groups, (7) a $C_7$-$C_{13}$ aralkyl group, (8) a 5 or 6 membered heterocycle containing an oxygen atom, and optionally substituted by one or two $C_1$-$C_4$ straight or branched chain alkyl groups, or (9) methyl substituted by a 5 or 6 membered heterocycle containing an oxygen atom and optionally substituted by one or two $C_1$-$C_4$ straight or branched chain alkyl groups and $R_5$ is hydrogen, a straight or branched chain $C_1$-$C_{20}$ alkyl group or a $C_5$-$C_6$ cycloalkyl group and with the proviso that the compounds of the following formulas are excluded

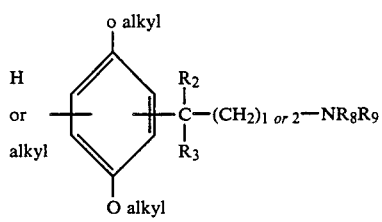

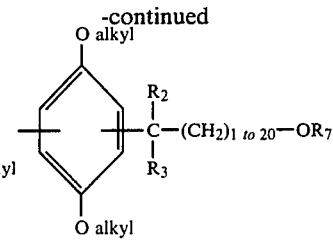

wherein $R_2$ and $R_3$ are as defined herein, $R_8$ and $R_9$ are H or alkyl and $R_7$ is H or alkyl; or a salt of compounds of formula I with a base or organic or inorganic acid, respectively, when Q is an acidic or basic group.

2. A compound of formula I according to claim 1 wherein the groups R and $R_1$ are bonded in the 2- and 5-positions, respectively, in the hydroquinone ethers of formula I or a salt thereof.

3. A compound of formula I according to claim 2 and having the formula VIII:

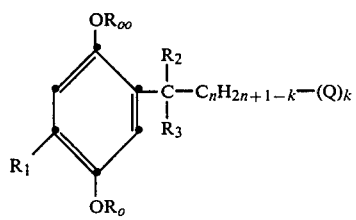

wherein $R_1$ is a group of formula II, or is a group of formula IX:

wherein G is $C_1$-$C_5$ alkyl or phenyl or a salt thereof.

4. A compound of formula VIII according to claim 3 wherein $R_1$ is as defined in claim 18, Q is —$OR_7$ and $R_2$ and $R_3$, independently, are methyl, ethyl, n-propyl, isopropyl or neopentyl.

5. A compound of formula VIII according to claim 4 wherein k is 1, n is an integer from 1 to 10 and $R_2$ and $R_3$, independently, are methyl, ethyl, or neopentyl.

6. A compound of formula VIII according to claim 5 wherein $R_7$ is hydrogen or $C_1$-$C_{15}$alkyl, and $R_o$ and $R_{oo}$ are hydrogen or $C_1$-$C_8$alkyl optionally interrupted by 1 or 2 oxygen atoms, cyclohexyl, phenyl or benzyl or $R_o$ and $R_1$ together form a residue of formula V or a salt thereof.

7. A compound of formula VIII according to claim 6 wherein $R_o$ and $R_{oo}$ are hydrogen or $C_1$-$C_4$ alkyl, or $R_o$ and $R_1$ together form a residue of formula V or a salt thereof.

8. A compound of formula VIII according to claim 7 wherein $R_7$ is $C_1$-$C_8$ alkyl or a salt thereof.

9. A compound of formula VIII according to claim 3 wherein one of $R_o$ and $R_{oo}$ is hydrogen, and the other is $C_1$-$C_4$ alkyl or $R_o$ and $R_1$ together form a residue of formula V.

10. A compound of formula XIV according to claim 1

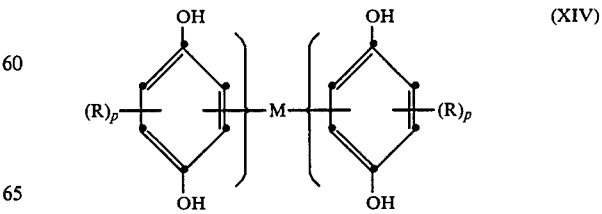

wherein R, M and p are as defined in claim 1.